(12) United States Patent
Kolsky et al.

(10) Patent No.: US 10,092,006 B2
(45) Date of Patent: Oct. 9, 2018

(54) STABLE COMPOSITIONS OF UNCOMPLEXED IODINE AND METHODS OF USE

(71) Applicant: ioTech International, Inc., Boynton Beach, FL (US)

(72) Inventors: Rodger Elliot Kolsky, Boynton Beach, FL (US); Herbert Moskowitz, Boynton Beach, FL (US); Jack Kessler, Southborough, MA (US)

(73) Assignee: ioTECH INTERNATIONAL, Boca Raton, FL (US)

( * ) Notice: Subject to any disclaimer, the term of this patent is extended or adjusted under 35 U.S.C. 154(b) by 0 days.

(21) Appl. No.: 15/128,556

(22) PCT Filed: Mar. 26, 2015

(86) PCT No.: PCT/US2015/022643
§ 371 (c)(1),
(2) Date: Sep. 23, 2016

(87) PCT Pub. No.: WO2015/153258
PCT Pub. Date: Oct. 8, 2015

(65) Prior Publication Data
US 2017/0208814 A1    Jul. 27, 2017

Related U.S. Application Data

(60) Provisional application No. 61/972,626, filed on Mar. 31, 2014.

(51) Int. Cl.
*A01N 59/12* (2006.01)
*A01N 37/02* (2006.01)
*A01N 31/02* (2006.01)
*A01N 59/00* (2006.01)
*A61K 33/18* (2006.01)
*A61K 9/00* (2006.01)
(Continued)

(52) U.S. Cl.
CPC ............... *A01N 59/12* (2013.01); *A23B 4/12* (2013.01); *A23B 4/20* (2013.01); *A23B 4/24* (2013.01); *A23B 7/10* (2013.01); *A23B 7/157* (2013.01); *A23L 3/349* (2013.01); *A23L 3/3508* (2013.01); *A23L 3/358* (2013.01); *A61K 9/0053* (2013.01); *A61K 33/18* (2013.01); *A61L 2/186* (2013.01); *C02F 1/50* (2013.01); *C02F 1/722* (2013.01); *C02F 1/766* (2013.01); *A23V 2002/00* (2013.01); *C02F 1/66* (2013.01); *C02F 2103/42* (2013.01); *C02F 2303/04* (2013.01)

(58) Field of Classification Search
CPC ........................................................ A61K 36/79
USPC ........................................................ 427/777
See application file for complete search history.

(56) References Cited

U.S. PATENT DOCUMENTS

| 2,918,400 A | 12/1959 | Loonam |
| 3,958,026 A * | 5/1976 | Leone ................. A23B 4/20 426/332 |

(Continued)

FOREIGN PATENT DOCUMENTS

| CN | 102670648 A | 9/2012 |
| WO | WO 96/24049 | 8/1996 |

(Continued)

OTHER PUBLICATIONS

Favero MS, Iodine—Champagne in a Tin Cup. Infection Control, 1982;3(1):30-32.

(Continued)

*Primary Examiner* — Walter E Webb
(74) *Attorney, Agent, or Firm* — Henry D. Coleman; R. Neil Sudol

(57) ABSTRACT

The present invention is directed to a composition in solution (often, an aqueous solution) which comprises a combination of molecular iodine ($I_2$) and an acceptable source of iodate ($IO_3$), and an acid (inorganic or organic), wherein iodide and iodate are present in the composition at a molar ratio of about 0.1 to about 25, the concentration of uncomplexed molecular iodine is a disinfectant, biocidal and/or antimicrobial (depending upon the end use of the composition) effective amount the concentration of acid in the composition is effective to provide a buffering pH in the composition ranging from about 1.5 to about 6.5. Compositions according to the present invention are storage stable for unexpectedly long periods of time (up to about 5 years), and find use as disinfecting solutions, as germicides and/or biocides (e.g. antiviral, antibacterial, antifungal, antispore etc.) for various surfaces and solutions including living and inanimate surfaces and are particularly useful because of their low cost, their reduced use of iodine, their activity (because of the high concentration of free molecular iodine in solution), their reduced environmental impact, their long term storage stability and their reduced toxicity. They also have particular utility in treating food surfaces to retard spoilage, increase useful shelf-life and minimize the human and economic cost of food waste. The compositions inactivate viruses, bacteria (both gram negative and positive), spores and fungi. Compositions according to the present invention may be used and stored in a variety of materials, given the substantial absence of corrosion (non-corrosive) these compositions display. Dental compositions (e.g. pre-procedure rinses and other compositions) and methods related thereto are also disclosed.

21 Claims, No Drawings

(51) Int. Cl.

| | |
|---|---|
| *A23L 3/358* | (2006.01) |
| *A23L 3/349* | (2006.01) |
| *A23L 3/3508* | (2006.01) |
| *A23B 4/24* | (2006.01) |
| *A23B 4/12* | (2006.01) |
| *A23B 4/20* | (2006.01) |
| *A23B 7/157* | (2006.01) |
| *A23B 7/10* | (2006.01) |
| *C02F 1/76* | (2006.01) |
| *C02F 1/72* | (2006.01) |
| *C02F 1/50* | (2006.01) |
| *A61L 2/18* | (2006.01) |
| *C02F 1/66* | (2006.01) |
| *C02F 103/42* | (2006.01) |

(56) References Cited

U.S. PATENT DOCUMENTS

| | | |
|---|---|---|
| 4,140,766 A | 2/1979 | Kalogris |
| 4,271,149 A | 6/1981 | Winicov et al. |
| 4,444,756 A | 4/1984 | Schluessler |
| 5,116,623 A | 5/1992 | Khan et al. |
| 5,256,701 A | 10/1993 | Tamura et al. |
| 5,629,024 A | 5/1997 | Kessler et al. |
| 5,643,608 A | 7/1997 | McKinzie et al. |
| 5,962,029 A | 10/1999 | Duan et al. |
| 6,015,836 A | 1/2000 | Martin |
| 2001/0056127 A1 | 12/2001 | Kessler |
| 2003/0109405 A1 | 6/2003 | Kellar et al. |
| 2007/0298126 A1* | 12/2007 | Kessler ............... A61K 31/724 424/667 |
| 2012/0121743 A1* | 5/2012 | Garnier ................. A61K 8/97 424/777 |

FOREIGN PATENT DOCUMENTS

| | | |
|---|---|---|
| WO | WO 99/21567 A1 | 5/1999 |
| WO | 2002023993 A2 | 3/2002 |
| WO | 0448288 A1 | 10/2004 |
| WO | WO 2008/005194 A2 | 1/2008 |

OTHER PUBLICATIONS

Gottardi W. Iodine and Disinfection: Theoretical Study on Mode of Action, Efficiency, Stability, and Analytical Aspects in the Aqueous System. Arch Pharm Pharm Med Chem, 1999;332:151-157.

Kessler J. Are there Side Effects when Using Supraphysiologic Levels of Iodine in Treatment Regimens?Elseviier, 2009;803-812.

Kessler JH. The Effect of Supraphysiologic Levels of Iodine on Patients with Cyclic Mastalgia. The Breast Journal, 2004;10(4)328-336.

Kessler J, Hooge D. Aqueous Iodine Equilibria in Mammalian Iodination Reactions. Thyroid, 2007;17(1):19-24.

Hickey J, et al. Control of the Amount of Free Molecular Iodine in Iodine Germicides. J Pharm Phermacol, 1997;49:1195-1199.

Duan Y, et al. Properties of an enzyme-based low-level iodine disinfectant. Journal of Hospital Infection, 1999;43:219-229.

Gottardi W. Iodine and disinfection: theoretical study on mode of action, efficiency, stability, and analytical aspects in the aqueous system. Arch Pharm, 1999;332(5):151-157.

Gottardi W. Potentiometrische Bestimmung der Gleichgewichtskonzentrationen an freiem und komplex gebundenem Iod in waBrigen Losungen von Polyvinylpyrrolidon-Iod (PVP-Iod). Fresenius Z Anal Chem, 1983;314:582-585.

Gottardi W. Iodine and Iodine Compounds. Disinfection, Sterilization, and Preservation. S.S. Block Editor, 1991:152-166.

Favero MS. Iodine-champagne in a tin cup. Infect Control, 1982;3(1):30-32.

Gottardi W. Redox potential and Germicidal Action of Aqueous Halogene Solutions. Abl. Bakt. Hyg. I Abt. Orig. B, 1980;170:422-430.

* cited by examiner

US 10,092,006 B2

STABLE COMPOSITIONS OF UNCOMPLEXED IODINE AND METHODS OF USE

RELATED APPLICATIONS

This application is a United States national phase patent application based upon international patent application number PCT/US2015/022643 filed 26 Mar. 2015, which claims the benefit of priority of U.S. provisional patent application No. 61/972,626 filed on Mar. 31, 2014. The entire contents of the two applications are hereby incorporated by reference herein.

FIELD OF THE INVENTION

The present invention is directed to compositions which comprise a combination of molecular iodine ($I_2$) and an acceptable source of iodate ($IO_3^-$), and an acid (inorganic or organic), wherein the iodate and the molecular iodine are present in the composition at a molar ratio of about 0.1 to about 25 to about 1.5 to about 5.0, often about 0.25 to about 10 to about 1.25 to 5.0, and about 1.0 to 7.5 to about 1.25 to 5.0 or about 1.25 to about 5.0 to about 1.5 to about 5.0, the concentration of uncomplexed molecular iodine is a disinfectant, biocide and/or antimicrobial (depending upon the end use of the composition) effective amount ranging from about 0.5 ppm to about 2500 ppm, often about 1 ppm to about 1000 ppm, about 10 pm to about 500 ppm, about 20 ppm to about 350 ppm and about 25 ppm to about 300 ppm, about 35 ppm to about 250 ppm, about 50 ppm to about 200 ppm, the concentration of acid in the composition is effective to provide a buffering pH in the composition ranging from about 1.5 to about 6.5 (often about 2.0 to about 6.5 within this range), preferably 2.0 to about 5.5, often about 2.0 to about 5.0). Compositions according to the present invention are storage stable for unexpectedly long periods of time (up to about 5 years, often for at least about 2-4 weeks, often 1 month or more as described herein), and find use as disinfectants, sanitizers, sterilants, sporicides. food spoilage deterrents and biocides that kill viruses, fungi, bacteria, spores, mold and all other known microbes, and are particularly useful because of their low cost, their reduced use of iodine, their activity (because of the high concentration of free molecular iodine in solution), their reduced environmental impact, their long term storage stability and their reduced toxicity. Compositions for treating and/or preventing viral, bacterial (both gram negative and positive), parasite, fungal and spore-based infections, especially including Norovirus, Poliovirus, Hepatitis A, *Klebsiella pneumonie, Staphyloccus aureus, Trichophyton mentagrophytes, Acinetobacter boumanni* and *Candida albicans* in subjects or patients in need and for treating surfaces, including keratinous and mucosal tissue surfaces and wounds, represent additional uses of the present invention. Compositions according to the present invention may be used and stored in a variety of embodiments, given the substantial absence of corrosion (non-corrosive) these compositions display.

BACKGROUND OF THE INVENTION

Elemental iodine ($I_2$) is a blue-black crystal with a high metallic luster that sublimes readily to generate a violet-colored vapor. In solution, the term "molecular iodine" has been used to refer to the $I_2$ molecule. Molecular iodine ($I_2$) is a hydrophobic molecule that is highly polarizable. The chemical reactivity of $I_2$ includes: addition to double bonds, oxidization of sulphydral groups, addition to activated aromatic groups and formation of N-iodo derivatives. However, iodine also reacts with water to form iodine species that exist in several different oxidation states; molecular iodine is unstable in water due to these reactions.

The term "iodine" has been, and continues to be used imprecisely in medical literature to refer to several different chemical entities and complicated formulations that contain diverse iodine species. The imprecise description of iodine compositions in the art may stem, in part, from ambiguous analytical characterizations. For example, thiosulfate titration is the most commonly used USP method to measure $I_2$ but this method also detects triiodide and hypoiodous acid in addition to molecular iodine ($I_2$). From this point forward the present application shall use the term "molecular iodine" ($I_2$) or "uncomplexed molecular iodine" when referring to the $I_2$ species in an aqueous environment.

In an aqueous environment iodine exists in several forms or species. These species include: iodide ($I^-$), molecular iodine ($I_2$), hypoiodous acid (HOI), iodate ($IO_3^-$), triiodide ($I_3^-$) and polyiodides (e.g., $I_5^-$ or $I_7^-$). These species have different physical and chemical properties. The instability of polyvinylpyrrolidone-iodine (PVP-I) or starch-iodine compositions is primarily caused by hydration of molecular iodine to form hypoiodous acid which ultimately leads to formation of iodate and loss of iodine atoms from the complex equilibrium that yields a very low concentration of uncomplexed molecular iodine. Uncomplexed molecular iodine is responsible for the biocidal activity of iodine germicides. The instability of molecular iodine in an aqueous environment is a primary formulation constraint that has influenced the development of all aqueous based iodine germicides that rely upon complexed molecular iodine.

Four basic formulation strategies have been used to overcome aqueous $I_2$ instability. These include: (a) the use of iodide as a complexing agent, (b) the use of organic complexing agents such as polyvinylpyrrolidone, starch and other complexing agents which complex $I_2$, (c) solid compositions that release elemental iodine slowly and (d) the use of oxidation reactions to produce iodine in situ. Each approach has inherent constraints and potential benefits that need to be evaluated in light of an intended application. However, adopting a formulation strategy that requires complexation of molecular iodine i.e., the two strategies identified as (a) and (b) above, necessarily require incorporation of considerably more iodine than an approach based on uncomplexed iodine in order to provide a similar biocidal capability.

Formulations based on iodine-complexation require additives that reduce the chemical activity of molecular iodine in a composition via the expedient of a relatively tight binding between said additive and molecular iodine. That is, the binding between complexing agent and molecular iodine must be tight enough to prevent hydration of molecular iodine. This approach results in a very low concentration of free or uncomplexed molecular iodine and a very high concentration of bound molecular iodine. As an example, commonly used 10% PVP-I typically delivers 2-4 ppm of unbound molecular iodine in a composition that contains over 15,000 ppm of total iodine atoms. The level of total iodine is obviously much higher than that amount of pure molecular iodine required for biocidal efficacy. Drawbacks of such compositions include undesirable toxicological properties, unwanted interactions with inanimate materials, increased costs and a higher environmental burden, as well as limited efficacy for many indications due to low concentrations of uncomplexed iodine and poor stability upon dilution.

U.S. Pat. No. 5,629,024 describes methods to generate molecular iodine in an aqueous environment, but the compositions described therein do not have a useful activated use-life because the molecular iodine is dissipated rapidly via reaction with water. Despite the fact that the compositions described in U.S. Pat. No. 5,629,024 patent do not require high levels of molecular iodine the patent does require generation of molecular iodine by the peroxysulfate anion at a controlled rate equal to the rate of loss of molecular iodine. Although this approach is viable, the method described in U.S. Pat. No. 5,629,024 is limited to applications where the loss of molecular iodine is equivalent to, or slightly greater than, the minimum generation rate of molecular iodine over the intended period of use. Additionally, the method described in U.S. Pat. No. 5,629,024 requires users to activate the composition of interest prior to use since it cannot provide a stable formulation that can be manufactured and placed into commercial distribution channels, resulting in unnecessary inconvenience and chance of operator error.

The use of iodate in iodophor compositions is a well-known formulation approach to one skilled in the art that is used to increase the stability of molecular iodine in these complex formulations. Winicov and Oberlander (U.S. Pat. No. 4,271,149) described methods to stabilize complexed iodine compositions via the use of an iodate ion in the range of about 0.005% to 0.2% within a pH range of pH 5-7. McKinzie and Winicov (U.S. Pat. No. 5,643,608) developed iodophors with high levels of molecular iodine using mixtures of iodine-iodide-iodate compositions with stability for 1 to 3 months which contained 0.005-0.5% iodate by weight in a pH range of about 2.0-4.5. Buxton et. al. (EP0448288 B1) describes the use of iodate in a concentration range of 0.01% to 0.04% in stabilized iodophors to provide reduced irritancy. Khan and Moellmer (U.S. Pat. No. 5,116,623) describe the use of periodate to stabilize iodophors. All of these patents described iodine formulations wherein the iodine is complexed and therefore the interaction of iodate in these iodide rich environments is not precisely controlled or predictable in contrast to the present invention.

The marketplace has shown a long-felt need for a storage stable, non-toxic germicide that can reduce transmission of infectious agents and inactivate resistant microbial strains. For example, microbial infections, from viruses, spores, bacteria, fungi, etc., for example, Norovirus infections, which induce stomach pain, nausea, diarrhea and vomiting, place a significant economic and health burden on society. Norovirus and other viruses and bacteria are transmitted by human contact, contaminated food or water, or by touching contaminated surfaces. Proper prevention techniques in the healthcare and food preparation workplace require repeated daily hand disinfection which can be problematic since efficacious hand sanitizers often cause irritation when used chronically. The same problem persists in hospitals with respect to the cause of nosocomial infections and resistant *staphylococcus* (MRSA) and *streptococcus* infections, among numerous others. A key objective of the formulations contemplated in this application is the rapid elimination (in some cases to unmeasurable numbers) of viruses, spores, bacteria and fungi such as norovirus and all resistant bacterial microbes, especially including, for example, multiple drug resistant staph infections (MRSA).

The annual economic cost of food spoilage to producers, processors, transporters, retailers and consumers is estimated to be $750 billion dollars globally. Approximately 1.3 billion tons of foods are wasted every year. This spoilage is primarily caused by the action of microbes on the surfaces of the affected foodstuffs (meats, berries, vegetables, fruits, seafood and grains). The compositions described in this application are suitable to both sanitize and extend the shelf life of many foods thereby providing a significant economic benefit.

SUMMARY OF THE INVENTION

The present invention describes compositions that provide formulations of uncomplexed molecular iodine that are stable, non-irritating, non-toxic and capable of being placed into commercial distribution channels with extended storage stability (months or years). In one embodiment, the compositions described in this application: (a) provide a constant thiosulfate titratable level of iodine over the shelf-life of the product and (b) exhibit a chemical activity of molecular iodine that is at least about 50% (at least about 55%, at least about 60%, at least about 65%, at least about 70%, at least about 75%, at least about 80%, at least about 85%, 90%, 95% or more) of an equivalent concentration of molecular iodine (based upon the total atoms of iodine) as measured potentiometrically in a 0.1N HCl solution. Thus, the present compositions provide an unexpectedly high level of activity of molecular iodine as an uncomplexed species, in a composition which is storage stable.

In other embodiments, the present invention describes compositions that contain uncomplexed molecular iodine in combination with complementary germicides that act to broaden the spectrum of activity and/or speed of action of said germicides, sometimes unexpectedly resulting in synergistic activity. Virtually any pathogen which can cause health problems can be eliminated from surfaces using compositions according to the present invention.

In contrast to the prior art, the present application describes germicidal compositions wherein the majority of molecular iodine is uncomplexed. Formulations based on iodine-complexation require additives that reduce the chemical activity of molecular iodine via the tight association required to stabilize molecular iodine. This complexation approach results in a very low chemical activity of free or uncomplexed molecular iodine and a very high concentration of bound molecular iodine, thus reducing the biocidal activity of the composition as a whole and requiring much higher levels of iodine to provide sufficient molecular iodine to function effectively. As an example, commonly used 10% PVP-I typically delivers 2-4 ppm of unbound molecular iodine in a composition that contains over 15,000 ppm of total iodine atoms. The level of total iodine is obviously much higher than that amount of uncomplexed molecular iodine required for biocidal efficacy. Drawbacks of such compositions include undesirable toxicological properties, unwanted interactions with inanimate materials, skin staining, increased costs, a higher environmental burden and lower efficacy per unit mass of iodine.

The present application contemplates a wide range of use applications. The use of uncomplexed iodine is desirable because the disinfectant/biocidal/antimicrobial activity of a composition can be optimized for a specific use even if that application requires high levels of such activity. The use of uncomplexed iodine is beneficial as compared to iodophors because (a) free, or uncomplexed, molecular iodine is the biocidal agent in all iodine-based germicides including iodophors whereas complexed iodine per se does not exhibit biocidal activity until it dissociates from its complexing agent providing free molecular iodine or $I_2$; (b) the complexing agents used in iodophors can interact with complementary biocides that could otherwise be added to an iodine-based germicide to increase its level or range of germicidal activity; (c) iodophors are more costly to produce, (d) uncomplexed iodine formulations can achieve higher levels of free molecular iodine with greater biocidal activity than iodophors, and (e) uncomplexed iodine formulations are substantially less toxic.

In one embodiment, the present invention is directed to a composition comprising an effective amount of a source of iodide (often from a soluble iodide salt such as sodium and/or potassium iodide, among others) and iodate (often from a soluble iodate salt such as sodium iodate, potassium iodate, calcium iodate, potassium hydrogen iodate, etc. or mixtures thereof) in solution wherein the molar ratio of iodide to iodate (which forms molecular iodine and therefore serves as a source of molecular iodine) is about 0.1 to about 25, often about 0.25 to about 10, often about 0.5 to about 7.5, about 1 to about 6.5, about 1 to about 5 or about 1.25 to about 5.0 and a predetermined amount of a buffering acid, wherein the acid is included in said composition in an amount which will provide a buffered pH within the range of about 1.5 to about 6.5, 1.5 and about 6.5, about 2.0 and about 6.0, about 2.5 to about 5.5, about 2.0 to about 5.0, wherein at least about 50% of the total amount of molecular iodine in the composition is uncomplexed and the concentration of uncomplexed molecular iodine in the composition ranges from about 0.5 ppm to about 2500 ppm, often about 1 ppm to about 1000 ppm, about 10 pm to about 500 ppm, about 20 ppm to about 350 ppm and about 25 ppm to about 300 ppm, about 35 ppm to about 250 ppm, about 50 ppm to about 200 ppm. These compositions generate molecule iodine which provides the principal antimicrobial activity. Compositions according to the present invention are capable of disinfecting surfaces, solutions (including water supplies such as swimming pools, municipal drinking sources, etc.) and/or otherwise eliminating microbes from surfaces to which the compositions are applied to a level of at least 99%, often at least 99.9%, often at least 99.99%, often at least 99.999%, often at least 99.9999%, often at least 99.99999%, and often more than 99.999999% to a level such that the microbes initially in solution or on the surface treated with compositions according to the present invention are beyond the capability of contemporary analysis (i.e., they are essentially eliminated from the surface treated with compositions according to the present invention).

Treatment of vegetables, fruits and other foods immediately prior to use presents a unique use case. In this case the vegetables, fruits or other foods may be treated; the iodine-based treatment composition may be discarded and the foods immediately eaten. The benefit of an extended shelf-life for the composition is not significant in this use case. Therefore, in this embodiment one preferred method for treatment can include in one embodiment, a composition comprising an effective amount of a source of iodide (often from a soluble iodide salt such as sodium and/or potassium iodide, among others) and iodate (often from a soluble iodate salt such as sodium iodate, potassium iodate, calcium iodate, potassium hydrogen iodate, etc. or mixtures thereof) wherein the molar ratio of iodide to iodate (which forms molecular iodine and therefore servers as a source of molecular iodine) is about 4.0-7.5 to about 1.0, often about 4.5-6.5 to about 1.0 and most often about 5.0 to about 1.0, wherein the acid is included in said composition in an amount which will provide a buffered pH within the range of about 1.0 and about 6.5, about, 1.5 and about 6.5, about 2.0 and about 6.0, about 2.5 to about 5.5, about 2.0 to about 5.0, about 1.0 to about 3.5 to about 4, wherein at least about 80% of the total amount of molecular iodine in the composition is uncomplexed and the concentration of uncomplexed molecular iodine in the composition ranges from about 1 ppm to about 500 ppm, about 10 ppm to about 150 ppm, often about 25 ppm to about 200 ppm and about 35 ppm to about 300 ppm. These compositions generate molecule iodine which provides the principal antimicrobial activity. In certain embodiments for the rapid generation of iodine within a period of no more than about several minutes (e.g. about 30 seconds to about 15 minutes, about 1 minutes to about 10 minutes, about 2 minutes to about 7.5 minutes, about 2 minutes to about 5 minutes) for disinfection of foodstuffs such as vegetables and fruits and the like, a preferred lower pH range of about 1.0 to about 3.5 to 4.0, or about 2.0 to about 4.0 is used along with a preferred molar ratio of iodide/iodate of about 5.0. Compositions according to the present invention are capable of eliminating microbes from surfaces of food to which the compositions are applied to a level of at least 99%, often at least 99.9%, often at least 99.99%, often at least 99.999%, often at least 99.9999%, often at least 99.99999%, and often more than 99.999999% to a level such that the microbes initially in solution or on the surface treated with compositions according to the present invention are beyond the capability of contemporary analysis (i.e., they are essentially eliminated from the surface treated with compositions according to the present invention). This includes virus such as norovirus.

In other embodiments of the present invention, the present compositions may include an effective amount of additional germicidal agents, including a peroxide compound, for example, hydrogen peroxide, or a per-oxygen compound, for example, peracetic acid, or an alcohol, for example, ethanol.

In certain embodiments, peracetic acid is preferably used in combination with the disinfectant compositions of the present invention for surface disinfection, especially hard surface disinfection. In these embodiments, the composition advantageously may employ a dual chamber dispensing system for combining/delivering peracetic acid along with the present distinfectant compositions onto a surface to be disinfected. Usable ranges of peracetic acid fall within the overall range of about 200 ppm to about 10,000 ppm. By nature, dilute peracetic acid is unstable, but has a useful commercial shelf life. Peracetic acid is typically supplied in concentrations of 5%, 15% and 35.5% solutions, each of which has about a one year shelf life (stability). Once diluted for use, these solutions become readily unstable. Some dilute fixed concentrations can be supplied, e.g. 1400 ppm or other lower concentrations, but shelf life of these solutions is questionable. Thus, another embodiment of the present invention is directed to a method to deliver peracetic acid in combination with the present compositions such that the peracetic acid solution is diluted only at the time of use. This embodiment comprises a two part container or two containers, the first of the two parts or containers comprising the storage stable concentrated peracetic acid solutions (e.g., a 5% solution) and the second of the two parts or containers comprising the composition according to the present invention which are delivered to the surface separately from the two parts or containers. It is noted that peracetic acid and molecular iodine and/or alcohol cannot be safely mixed (potential strong reaction between the peracetic acid and the alcohol and/or iodine) and even if they could, the peracetic acid dilution would result in instability and reduce the shelf life of the composition. A number of dispensing systems may be used in this aspect of the invention. For example, the dispensing system used in this embodiment comprises an off the shelf dual compartment sprayer which proportions the components at the time of delivery from the spray head, or alternatively, the system comprises two bottles with tubing connected to two separate spray heads or two tubes from two bottles using different diameters to meter the liquids both of which are connected to a single spray head.

In still other embodiments, the present compositions further comprise effective amounts of additional components selected from non-aqueous solvents (ethanol, isopropanol, n-propanol, etc.) surfactants, emulsifiers, including secondary emulsifiers, emollients, oils, humectants, oils (polar and non-polar), conditioning agents, thickeners/thickening agents, medicaments, fragrances, preservatives, skin protecting agents, pigments, dyes, coloring agents, gelling agents and mixtures thereof in order to provide compositions exhibiting characteristics consistent with the use of the compositions, depending upon the surface to be treated, which surfaces include biological surfaces especially including keratinous and mucosal tissue and/or wounds of an animal, including a human.

In other embodiments the composition according to the present invention is directed to a gel or thickened composition for human and veterinary uses especially for periodontal uses, i.e., in periodontal applications, especially including the treatment and disinfection of periodontal surfaces, including before and after oral surgery and the like. In this embodiment, the gel or thickened composition is placed in contact with periodontal surfaces by means of a tray, syringe, infusion or similar approach which exposes the periodontal surface to the composition. In still other embodiments, a liquid composition is provided as a dental wash, rinse or irrigant for human and veterinary applications, including to reduce mouth odor and/or to reduce (knock down) potential bacterial load in the mouth of a subject to whom the rinse is applied. In one embodiment, the present invention provides an iodine containing mouthwash as a dental preprocedure rinse. This mouthwash is advantageously used by dental patients prior to any procedure (e.g., a treatment procedure including a surgery, dental cleaning and/or prophylaxis) to reduce or knock down the microbial load to help reduce the likelihood (prevent) disease transmission from the patient to the dental staff, for example, when the microbes become aerosolized due to water spray, air spray, ultrasonic instrumentation or the spray from a high speed hand piece utilized in dental procedures. In this embodiment, the concentration of molecular iodine ranges from about 3 to about 350 ppm, often about 5 to about 200 ppm, more often about 10 to about 100 ppm.

In still other embodiments, a gelled composition is provided which may further include packaging such as in a semi-permeable pouch or other packaging to allow delivery of iodine vapor from the composition enclosed therein at a controlled rate to kill mold and bacteria in a food or other sample, for example, in a container of berries or other food item. In this embodiment, for example, a small semi-permeable pouch or other packaging which is adapted to allow the release of iodine vapor from the composition could be placed in a container with food items (often fruits and/or vegetables) to be treated, the container being preferably sealed to prevent or inhibit the release of iodine vapor during the treatment of the food items. In this application, the small pouch or other packaged composition could be placed in the container in contrast to immersing the food items in an aqueous solution of iodine.

In further embodiments, the present invention is directed to methods of disinfecting a solution or a surface, including a biological surface comprising exposing a solution or surface to be disinfected with an effective amount of a composition according to the present invention. Methods according to the present invention may be used to disinfect surfaces, including biological surfaces including hands, and skin areas to be disinfected after a wound to disinfectant the wound, before a medical procedure (e.g. surgery) and other use indications (for example, treatment of hard surfaces on which food is prepared) such that numerous microbes are substantially eliminated and/or inhibited from growing on the exposed surface. Methods of disinfection may be used to disinfect surfaces from a variety of microbes, including viruses, bacteria, fungi, spores, mold, parasites and prions, among others, as otherwise described herein.

Definitions

The following terms are used to describe the present invention. In instances where a term is left undefined, the term is given its art recognized meaning. In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

The term "compound", as used herein, unless otherwise indicated, refers to any specific chemical compound disclosed herein. Within its use in context, the term generally refers to a single compound as otherwise described herein. Compounds which are disclosed are those which are stable.

The term "patient or subject" is used to describe an animal, including a domesticated animal (such as a domesticated bird, a dog, cat, cow, horse, pig, sheep, goat, fish, etc.) especially including a mammal, especially a human to which compositions according to the present invention may be applied.

The term "effective" is used, in context, to describe an amount or concentration of a compound, composition or component, as otherwise described herein which is included or used to provide an intended effect or trait as otherwise described in context, such as disinfection, biocidal and/or antimicrobial activity, or other attribute, such as buffering effect, depending upon the final composition, or an effect or trait dependent upon the nature of the final product such as surfactancy, emulsification (emulsifiers), emolliency, wetability, skin adherence, storage stability, and/or solubility to a formulation or to produce a compound or composition according to the present invention. It is noted that when the term "effective" is used within the context of disinfecting a surface with a composition according to the present invention, this term is used to describe an effective amount of the composition containing an effective amount of uncomplexed molecular iodine which is contacted with the surface to be disinfected for a period of time and at a temperature (often at room temperature, but in certain embodiments at elevated temperatures such as at 37 degrees to about 50 degrees C. or more, including in certain embodiments with spores and mold, among others) sufficient to disinfect the surface.

The term "source of iodide" is used to describe a compound or material which is generally, an iodide salt, which provides an effective concentration of iodide anion in solution which is used in compositions according to the present invention. The source of iodide used in compositions according to the present invention includes any appropriate source of iodide, especially iodide salts (and includes hydroiodic acid) which dissociate when placed in solution. Preferred sources of iodide for use in the present invention include NaI (sodium iodide), KI (potassium iodide), LiI (lithium iodide), $CaI_2$ (calcium iodide) and $MgI_2$ (magnesium iodide), among others.

The term "source of iodate" is used to describe an appropriate compound or material (generally, an iodate salt), which provides a concentration of iodate anion in solution which is used in the present invention. The source of iodate used in compositions according to the present invention includes any appropriate source of iodate, especially iodate salts which dissociate when placed in solution. Preferred sources of iodate for use in the present invention include $NaIO_3$ (sodium iodate), $KIO_3$ (potassium iodate), $LiIO_3$ (lithium iodate), $CaIO_3$ (calcium iodate) and $MgIO_3$ (magnesium iodate), among others.

The term "disinfect" shall mean eliminating microbes from surfaces to which the compositions are applied or solutions in which the compositions are added to a level of at least about 99%, often at least about 99.9%, often at least about 99.99%, often at least about 99.999%, often at least about 99.9999%, often at least about 99.99999%, and often more than about 99.999999 (the remaining population of microbes is less than about $10^{-6}$), 99.9999999 (the remaining population of microbes is less than about $10^{-7}$) or 99.99999999% (the remaining population of microbes is less than about $10^{-8}$) or even lower, including to a level such that the microbes initially in solution or on the surface treated with compositions according to the present invention are eliminated to a level beyond the capability of contemporary analysis (i.e., they are essentially eliminated from the surface treated with compositions according to the present invention).

The term "surface" shall mean any surface to which compositions according to the present invention are applied. The surface is any surface for which the present compositions may be used for their disinfectant, antimicrobial and/or biocidal activity, for example, any inanimate surface such as the surface of a floor, countertop, table, furniture, any surface which comes in contact with food or the surface of the food itself, medical and/or surgical equipment or a surface or a keratinous surface such as the skin, hair or nails (ungual) or mucosal surface (including internal surfaces of an animal or human, such as the throat, mouth (including teeth and/or gums) or nasal passages or other mucosal surfaces in the body including the ears, vagina or internal surfaces in an animal, including a human) or a wound of a patient or subject. In certain applications, the compositions may be used internally in a patient or subject, for example, pursuant to medical procedures. In other applications, the compositions are used to disinfect the hands and/or other body surfaces of a subject or patient, including skin surfaces in which incisions are to be made pursuant to surgical procedures. In certain important applications associated with food preparation, compositions according to the present invention are applied to any surface where food is stored and/or prepared or to the hands or other surfaces of individuals who are engaged in food preparation or to the surfaces of the food itself. Other important applications include direct application to mucosal and subgingival surfaces, ear drops and toothpaste. In addition, it is anticipated that the compositions described herein shall be directly applied to mucosal surfaces, e.g. douche, oral irrigation, lavage, oral ingestion, throat spray or gargle, nasal/sinus spray or mouthwash.

The term "molecular iodine" or "uncomplexed molecular iodine" as used herein, refers to diatomic iodine, which is a molecule comprised of 2 iodine atoms and is represented by the chemical symbol $I_2$ (CAS Registry Number: 7553-56-2). Some of the prior art uses the term "elemental iodine" to describe the same chemical entity.

The term "iodide" or "iodide anion" refers to the anion that is represented by the chemical symbol $I^-$ (CAS Registry Number: 20461-54-5). For instance, the iodide anion forms when a salt of iodine is dissolved in water. Suitable counterions for the iodide anion include sodium, potassium, calcium, magnesium and the like.

The term "chemical activity" refers to a measure of the effective concentration of molecular iodine when in the presence of other chemical species. The difference between the chemical activity of molecular iodine and the concentration of molecular iodine in iodophors is largely a measure of complexation of molecular iodine in iodophors.

The term "uncomplexed molecular iodine" or "free molecular iodine" refers to molecular iodine which is in free form. In compositions according to the present invention at least about 50% (at least about 55%, at least about 60%, at least about 65%, at least about 70%, at least about 75%, at least about 80%, at least about 85%, 90%, 95% or more) of the total iodine species present are in uncomplexed molecular form and contribute to the chemical activity of molecular iodine as compared to a pure composition of molecular iodine in a 0.1N HCl solution as measured by the potentiometric method of Gottardi (Gottardi, W., *Iodine and disinfection: theoretical study on mode of action, efficiency, stability, and analytical aspects in the aqueous system*. Arch Pharm, 1999. 332 (5): p. 151-157; Fresenius Z Anal Chem 1983:314; p. 582-5).

The term "thiosulfate titratable iodine" as used herein, refers to all iodine species that can be titrated with sodium thiosulfate including molecular iodine, triiodide, hypoiodous acid and polyiodides.

The term "triiodide" refers to a molecule formed by the interaction of an iodide anion with molecular iodine in an aqueous solution. The triiodide species (I3) consists of 3 iodine atoms and has a net negative charge. Triiodide per se is not a biocide and therefore does not directly contribute to biocidal activity in compositions according to the present invention.

The term "total iodine" as used herein, refers to the sum of iodine atoms in the following species: iodide, molecular iodine, hypoiodous acid, and all other forms of thiosulfate titratable iodine which are present in a composition.

The term "iodate" or "iodate anion" refers to the anion that is the conjugate base of iodic acid wherein an atom of iodine is bonded to three oxygen atoms. Iodate is represented by the chemical symbol $IO_3^-$ (CAS Registry Number: 15454-31-6).

In the present invention, iodate generates molecular (uncomplexed) iodine within the composition for use as a disinfectant/biocide/antimicrobial pursuant to the present invention. By relying on iodate to produce uncomplexed molecular iodine on an ongoing basis, the concentration of uncomplexed molecular iodine within the present composition, remains within a range of concentration which maximizes biocidal/germicidal and disinfectant activity for unexpectedly long periods of time. For example, depending upon the amount of acid and the buffered pH of the composition (note that a lower pH within the range of the present compositions will tend to result in greater stability and a more efficient formation of molecular iodine from iodate than a higher pH), from at least a week to about 5 years, about two-three weeks to about 3-4 years, about a month to about 2-2.5 years, or at least 3-6 months to a year within this range.

The term "molar ratio of molecular iodine to iodate" or vice versa refers to the molar ratio of molecular iodine molecules to iodate anions (or vice versa) in a composition.

The term "ratio of molecular iodine to total iodine" in a substance as used herein, refers to the ratio of the total amount of molecular iodine in a composition of matter divided by the total iodine in the substance.

The term "molar excess of iodate to molecular iodine" in a formulation as used herein refers to refers to the molar ratio of iodate to uncomplexed molecular iodine in a composition which is above a 1:1 molar ratio.

The term "molar excess of iodate to iodide" or "molar excess of iodate" refers to that increment of a molar ratio of iodate to iodide anion in a solution above a stoichiometric ratio of 1:1; for example, if the stoichiometric ratio is 5 moles of iodate for every 1 moles of iodide, the molar excess of iodate to iodide is 4 in this example. By way of further example, if the molar ratio is 1.25 to 1 (iodate to iodide), the molar excess of iodate is 0.25. For the purposes of this application, an effective molar excess of iodate can be achieved by adding iodate directly to a composition that contains molecular iodine, e.g. after a stoichiometric ratio of iodide/iodate has reacted to form molecular iodine. In compositions according to the present application, the molar ratio of iodate to iodide falls within the range of about 0.1 to about 25, often about 0.25 to about 10 to about 1.25 to 5.0, and about 1.0 to 7.5 to about 1.25 to 5.0 or about 1.25 to about 5.0 to about 1.5 to about 5.0 depending upon the final concentration of uncomplexed (free) molecular iodine desired and the duration of stability of the composition in providing that concentration of that uncomplexed molecular iodine.

The term "buffer" or "buffering acid" is used to describe any compatible inorganic or organic acid which is capable of maintaining a pH of compositions according to the present invention within the range of about 1.0 to about 6.5, about 1.5 to about 6.5, about 2.0 to about 5.5, about 2.0 to about 5.0, about 1.0 to about 3.5-4.0 with a preferred range of about 2.0 to about 4.0. The preferred pH of the compositions contemplated in the current invention will vary based upon the use regimen for an application. If it is necessary or desirable to generate molecular iodine instantly or in a short time after admixing the actives of this invention the desired pH range if pH 2 to pH 4 with an preferred pH range of pH 2 to pH 3. If a composition will be activated but not used immediately but rather used after a delay, then the preferred pH range can extend to 6.5. Preferred acids for use in the present invention include mono or polyacids which provide a buffering effect to maintain the pH of compositions according to the present invention within the range of pH, and includes such acidic entities as phosphate acids (including polyphosphate acids), such as phosphoric acid and its related salts sodium dihydrogen phosphate and sodium monohydrogen phosphate, polyphosphoric acid ($H_{n+2}P_nO_{3n+1}$), organic acids having from two to 20 or more carbon atoms, including acids according to the chemical structure $R—CO_2H$, where R is an optionally substituted (often with one or more hydroxyl groups) $C_1$-$C_{20}$ alkyl, alkenyl, alkynyl, aryl or other carbon containing group optionally having more than one double bond, preferably $C_1$-$C_{10}$ or organic acids or organic acids containing more than one carboxylic acid moiety (polycarboxlic acids) such as citric acid, oxalic acid, succinic acid, fumaric acid, malonic acid, maleic acid and various sulphonic acids according to the chemical structure $R_1—SO_3H$, where $R_1$ is a $C_1$-$C_{20}$ alkyl or aryl group which may be optionally substituted. Organic acids which may be preferred for use in the present invention include, for example, citric, fumaric, glycolic, lactic, malic, tartaric, acetic, formic, oxalic acid, propanoic, propandioic, butanoic, butanedioic, pentanoic (valeric), pentandioic, hexanoic, hexandioic and benzoic, among others. Other acids which also may be used include, for example, acids of bisulfate (sodium, potassium bisulfate), sulfamic acid, and ethylenediaminetetraacetic acid, among others. The use of citric acid, phosphoric acid or other polyacids may be preferred because of the ability of these acids to accommodate a number of hydrogen ions in a single chemical entity, which may assist in maintaining the pH of compositions according to the present invention within a relatively narrow buffered range, thus maintaining activity and stability of the present compositions. A particularly preferred acid, citric acid, refers to the free acid or monobasic (e.g. sodium salt) form of 2-hydroxypropane-1,2,3-tricarboxylic acid (CAS Registry Number: 77-92-9). Compositions anticipated in the present invention can incorporate the di- and tribasic forms of citric acid provided there is an effective amount of the free acid in order to insure that the pH of the compositions lie within a range from about 1.5 to about 6.5, often about 2.0 to 5.5, most often about 2.0 to about 5.0.

The term "activated use-life" as used herein, refers to the length of time an iodine-based disinfectant/biocidal/antimicrobial product maintains its initial activated (immediately post activation) level of the desired level of thiosulfate titratable iodine when stored under defined conditions. For instance, the activated use-life for an uncomplexed iodine germicide contemplated in this application may be an hour or a year or more (up to about 5 years) from the time of formulation. The term "stable" as defined herein refers to a composition according to the present invention that can be placed into normal distribution channels used in commerce which requires a minimum activated use-life of at least 1 week, or 1 month and preferably at least 4 to 6 months and most preferably with a activated use-life of 2-5 years with no substantial loss of thiosulfate titratable iodine-thereby maintaining activity as a disinfectant/germicide/biocide/antimicrobial composition.

The term "combined iodine-based germicide" as defined herein means an uncomplexed iodine germicide in combination with a complementary germicide or germicides such as peracetic acid, hydrogen peroxide or benzoyl peroxide alone or in combination with other compatible germicidal agents as otherwise described in the present application.

It is noted that used in this specification, the singular forms "a," "an," and "the" include plural references unless the context clearly dictates otherwise. Thus, for example, reference to a "source of iodine" includes a single source as well as two or more different sources, reference to an "active" refers to a single as well as to two or different actives, reference to an "inert" includes a single excipient as well as two or more different inerts, and the like.

The term "antimicrobial" refers to the fact that compositions according to the present invention often display activity against a broad range of viruses, bacteria, fungi, spores, mycobacteria, parasites, prions and other microbes.

The term "antiviral" is used to describe compositions according to the present invention which display general antiviral activity against viruses including animal, plant, fungal and bacterial viruses. Viruses which may be inhibited and/or eliminated pursuant to the methods according to the present invention using compositions disclosed herein include those which impact animals, especially mammals, and in particular humans, fish, domestic animals and include, for example, papovaviruses, e.g. Polyoma virus and sv40; poxviruses, e.g. Vaccinia virus and variola (smallpox); adenoviruses, e.g., human adenovirus; herpesviruses, e. G. Human herpes simplex types i and ii; parvoviruses, e.g. Adeno associated virus (aav); reoviruses, e.g., rotavirus and reovirus of humans; picornaviruses, e.g. Poliovirus; togaviruses, including the alpha viruses (group a), e.g. Sindbis virus and semliki forest virus (sfv) and the flaviviruses (group b), e.g. Dengue virus, yellow fever virus and the St. Louis encephalitis virus; retroviruses, e. G. Hiv i and ii, rous sarcoma virus (rsv), and mouse leukemia viruses; rhabdoviruses, e.g. Vesicular stomatitis virus (vsv) and rabies virus; paramyxoviruses, e.g. Mumps virus, measles virus and sendai virus; arena viruses, e.g., lassa virus; bunyaviruses, e.g., bunyawere (encephalitis); coronaviruses, e.g. common cold (rhinovirus), GI distress viruses, orthomyxovirus, e.g., influenza; caliciviruses, e.g., norwak virus, hepatitis e virus; filoviruses, e.g., ebola virus and marburg virus; and astroviruses, e.g. Astrovirus, among others. Virtually all viruses are susceptible to compositions according to the present invention.

Viruses such as influenza (especially H5N1 influenza), Herpes Simplex Virus (HSV1 and HSV-2), Coxsackie virus, Human immunodeficiency virus (I and II), Andes virus, Dengue virus, Papilloma, Epstein-Barr virus (mononucleosis), Variola (smallpox) and other pox viruses, West Nile virus, influenza (H5N1) are relevant targets for antimicrobial action of compositions according to the present invention.

A short list of animal viruses that may be relevant targets of compositions according to the present invention include:
  Norovirus
  Reovirus
  Rotavirus
  Aphthovirus
  Parechovirus
  Erbovirus
  Kobuvirus
  Teschovirus
  Enterovirus
  Rhinovirus
  Hepatovirus
  Hepatitis E virus
  Rubella virus
  Lymphocytic choriomeningitis virus
  HIV-1, HIV-2,
  HTLV-I
  Herpes Simplex Virus 1 and 2
  Cardiovirus
  Norwalk virus
  Influenzavirus A, B and C
  Isavirus,
  Thogotovirus
  Coxsackie Virus
  Dengue virus
  Yellow fever virus
  Hepatitis A virus
  Hepatitis B virus
  Hepatitis C virus
  Measles virus
  Mumps virus
  Respiratory syncytial virus
  California encephalitis virus
  Hantavirus
  Rabies virus
  Ebola virus
  Marburg virus
  Corona virus
  Astrovirus
  Borna disease virus
  Variola (smallpox virus)

Plant viruses also are relevant targets of compositions according to the present invention. The present invention may be used to disinfect, eliminate and/or inhibit the growth of plant viruses, especially in certain agricultural applications, especially including food production.

Plant viruses, which may serve as targets for the present invention include the following:

Partitiviruses, e.g., alphacryptoviruses and betacryptoviruses; Potyviruses, e.g., bymoviruses and ipomoviruses; Bromoviruses, e.g. cucumoviruses and bromoviruses; Comoviruses, e.g. fabiviruses, neopoviruses and comoviruses; Geminiviruses e.g., bigeminivirus, monogeminivirus and bybrigeminivirus; Rhabodoviruses, e.g., cytorhabdoviruses, nucleorhabdoviruses; Reoviruses, e.g., oryzaviruses and phytoreoviruses; Satellite viruses, e.g., satelliviruses; Tombusviruses, e.g., carmoviruses; Sequiviruses, e.g., sequiviruses and waikaviruses; among numerous others, including those listed hereinbelow.

Plant Virus Genuses which are targets of the present compositions and methods, include the following:
  Alfamoviruses: Bromoviridae
  Alphacryptoviruses: Partitiviridae
  Badnaviruses
  Betacryptoviruses: Partitiviridae
  Bigeminiviruses: Geminiviridae
  Bromoviruses: Bromoviridae
  Bymoviruses: Potyviridae
  Capilloviruses
  Carlaviruses
  Carmoviruses: Tombusviridae
  Caulimoviruses
  Closteroviruses
  Comoviruses: Comoviridae
  Cucumoviruses: Bromoviridae
  Cytorhabdoviruses: Rhabdoviridae
  Dianthoviruses
  Enamoviruses
  Fabaviruses: Comoviridae
  Fijiviruses: Reoviridae Furoviruses
Hordeiviruses
Hybrigeminiviruses: Geminiviridae
Idaeoviruses
Ilarviruses: Bromoviridae
Ipomoviruses: Potyviridae
Luteoviruses
Machlomoviruses
Macluraviruses
Marafiviruses
Monogeminiviruses: Geminiviridae
Nanaviruses
Necroviruses
Nepoviruses: Comoviridae
Nucleorhabdoviruses: Rhabdoviridae
Oryzaviruses: Reoviridae
Ourmiaviruses
Phytoreoviruses: Reoviridae
Potexviruses
Potyviruses: Potyviridae
Rymoviruses: Potyviridae
Satellite RNAs
Satelliviruses
Sequiviruses: Sequiviridae
Sobemoviruses
Tenuiviruses
Tobamoviruses
Tobraviruses
Tombusviruses: Tombusviridae
Tospoviruses: Bunyaviridae
Trichoviruses
Tymoviruses
Umbraviruses
Unassigned potyviruses: Potyviridae
Unassigned rhabdoviruses: Rhabdoviridae
Varicosaviruses
Waikaviruses: Sequiviridae
Ungrouped viruses The term "antibacterial" may also be used to describe compositions according to the present invention. Accordingly, the compositions according to the present invention may be used as antibacterial agents. The compositions are useful to eliminate or disinfect numerous types of bacteria, including gram negative and gram positive bacteria, especially including drug and multidrug resistant bacteria, including MRSA. A list of bacteria which are targets of the antimicrobial activity of compositions according to the present invention include:

Gram positive and gram negative bacteria including cocci and bacilli including for example:
Gram Positive:
  Staph aureus;
  S. epidermidis;
  S. saphrophyticus;
  S. haemolyticus;
  S. hominis;
  S. capitis S. schleiferi;
  S. warneri;
  S. lugdenenis;
  Strep pyrogenes (gr. A);
  S. agalactiae (gr. B);
  E. faecalis;
  E. faecium;
  Enterococci;
  S. pneumoniae;
  S. mutans group;
  S. salivarus group;
  S. sanguis group;
  S. mitis group;
  S. angiosus group
  Abiotrophica defective;
  A. adiacens;
  S. milleri;
  S. bovis;
  N. gonorrhea;
  N. meningitides;
  Moraxella catarrhalis;
  C. diptheriae;
  C. jeikenium;
  C. urealyticum;
  Lactobacillus sp.;
  Bacillus anthracis;
  B. cereus;
  Listeria monocytogenes;
  Erisipelothrix rhusiopathiae;
  Arcanobacterium bemolyticum;
Gram Negative;
  Escherichia coli;
  Klebsiella pneumoniae;
  Proteus spp.;
  Morganella;
  Providencia;
  Salmonella enterica;
  Shigella boydii (serogroup C);
  S. dysenteriae (serogroup A);
  S. flexneri;
  S. sonnei (serogroup D);
  C. freundii;
  C. koseri;
  Enterobacter cloacae;
  E. aerogenes;
  S. marcecescens;
  Vibrio cholera;
  V. parahaemolyticus;
  V. vulificans;
  Aeromonas hydrophila;
  Plesiomonas shigelloides;
  Acinetobacter baumannii;
  A. lowfii;
  Stenotrophomonas maltophilia;
  Pseudomonas sp;
  Pseudomonas aeruginosa;
  P. fluroescens;
  P. putida;
  Burkholderia cepacia;
  Alkaligenes;
  Haemophilus;
  H. influenzae;
  H. parainfluenzae;
  H. duceyi;
  HACEK group;
  Haemophilus aphrophilus;
  Actinobacter actinomysetemcomitans;
  Cariobacter hominis;
  Eikenella corrodens;
  Kingella kingii;
  Bordatella pertussis;
  Pasteurella multocida;
  Brucella sp.;
  Campylobacter;
  C. jejuni
  C. coli;
  C. fetus;
  Capnocytophaga;

*Francisella tularensis;*
*Helicobacter pylori;*
*Legionella pneumophila;*
*Mycoplasma pneumoniae;*
*M. hominis;*
*Ureaplasma urealyticum;*
*Bacteroides fragilis* group;
*B. fragilis;*
*B. distansonis;*
*B. thetaiotaomicron;*
*B. uniformis;*
*Proteus vulgaris;*
*B. ovatus;*
*B. uniformis;*
*Bacteroides* sp;
*B. ureolyticus*
*Bilophila wadsworthia*
*Porphyromonas* species;
*Prevotella;*
*Fusobacterium;*
*Clostridium* sp;
*C. perfringens;*
*C. botulinum;*
*C. tetani;*
*C. septicum;*
*C. difficile;*
*Actinomyces israeli;*
*Propionibacterium acnes;*
*Eubacterium;*
*Lactobacillus* sp.;
*Bifidobacterium;*
*Veillonella;*
*Peptostreptococcus;*
*Peptococcus*

The compositions according to the present invention may be used as antifungal agents. The compositions are useful to eliminate or disinfect numerous types of disease causing fungi including *Aspergillus, Coccidioides, Histoplasma capsulatum* and *Candida*, especially including *Candida albicans*, among others.

The present invention may also be used to inhibit and/or eliminate spores and mold. The term "spores" is used throughout the specification to describe a unit of asexual reproduction and/or resistance of many plants, algae, fungi, bacteria and protozoa that are adapted survival and dispersal of these organisms in unfavorable conditions. Spores are usually unicellular and under favorable conditions can develop into a new organism. Spores may be characterized more specifically as sporangiospores from fungi, zygospores from fungi, ascospores from ascomycetes, basidiospores from basidiomycetes, aeciospores, teliospores and uredeiospores from fungi such as rusts or smuts, oospores from oomycetes, carpospores and tetraspores from red algae. The term spores also includes meiospores, microspores, megaspores, mitospores, zoospores, aplanospores, autospores, ballistospores and statismospores, among others. The present invention may be used to substantially inhibit and/or eliminate spores from numerous surfaces in numerous applications as otherwise described herein.

The term "mold" is used to describe a fungus that grows in the form of multicellular filaments called hyphae. Molds are a large and taxonomically diverse number of fungal species where the growth of hyphae results in discoloration and a fuzzy appearance, especially on food. Molds are considered to be microbes and do not form a specific taxonomic or phylogenetic groups, but can found in the divisions of Zygomycota and Ascomycota. Molds often cause biodegradation of natural materials, which can be unwanted when it becomes food spoilage and/or damage to property. Molds also cause disease in animals and humans often resulting from allergic sensitivity to mold spores, from growth of pathogenic molds within the body, or from the effects of ingested or inhaled toxic compounds (mycotoxins) produced by molds.

There are thousands of known species of molds, which have diverse life-styles including aprotrophs, mesophiles, psychrophiles and thermophiles and a very few opportunistic pathogens of humans. They all require moisture for growth and some live in aquatic environments. Like all fungi, molds derive energy from the organic matter on which they live, utilizing heterotrophy. Typically, molds secrete hydrolytic enzymes, which degrade complex biopolymers such as starch, cellulose and lignin into simpler substances which can be absorbed. In this way molds play a major role in causing decomposition of organic material, enabling the recycling of nutrients. Molds often grow on stored food for animals and humans, making the food unpalatable or toxic and are thus a major source of food losses and illness. Many prior art strategies (salting, pickling, jams, bottling, freezing, drying) are used to prevent or slow mold growth as well as growth of other microbes. Molds reproduce by producing large numbers of small spores, which can be inhibited and/or eliminated by the compositions according to the present invention. Common molds include *Acremonium, Alternaria, Aspergillus, Cladosporium, Fusarium, Mucor, Penicillium, Rhizopus, Trichoderma* and *Stachybotrys*, among others. The present invention is useful to inhibit and/or eliminate each of these molds from surfaces on or in solutions in which they are present.

Prions are another class of important bioagents which may be eliminated or disinfected using the invention of the present application. Exemplary prions include Scrapie (Sheep and goats), transmissible mink encephalopathy (TME), chronic wasting disease (CWD) in mule deer and elk, bovine spongiform encephalopathy (BSE) cattle, feline spongiform encephalopathy (FSE) in cats, exotic ungulate encephalopathy (EUE), Kuru in humans, Creutzfeldt-Jakob disease (CJD) in humans, Fatal familial insomnia (FFI) in humans and Gerstmann-Sträussler-Scheinker syndrome (GSS) in humans.

Parasites are another class of important bioagents which may be eliminated or disinfected using the invention of the present application. Exemplary parasites which are disinfected (eliminated) by compositions according to the present invention include the following:

Alveolar Echinococcosis (Echinococcosis, Hydatid Disease)
Angiostrongyliasis (*Angiostrongylus* Infection)
Anisakiasis (*Anisakis* Infection, *Pseudoterranova* Infection)
Ascariasis (*Ascaris* Infection, Intestinal Roundworms)
Babesiosis (*Babesia* Infection)
Balantidiasis (*Balantidium* Infection)
*Balamuthia*
Baylisascariasis (*Baylisascaris* Infection, Raccoon Roundworm)
*Blastocystis hominis* Infection
Cercarial Dermatitis (Swimmer's Itch)
Chagas Disease (American Trypanosomiasis)
*Chilomastix mesnili* Infection (Nonpathogenic [Harmless] Intestinal Protozoa)
Clonorchiasis (*Clonorchis* Infection)
Cryptosporidiosis (*Cryptosporidium* Infection)
Cyclosporiasis (*Cyclospora* Infection)

Cysticercosis (Neurocysticercosis)
Cystoisospora Infection (Cystoisosporiasis) formerly *Isospora* Infection
*Dientamoeba fragilis* Infection
Diphyllobothriasis (*Diphyllobothrium* Infection)
Dirofilariasis (*Dirofilaria* Infection)
DPDx
Fasciolopsiasis (*Fasciolopsis* Infection)
Foodborne Diseases
Kala-azar (Leishmaniasis, *Leishmania* Infection)
Keratitis (*Acanthamoeba* Infection)
Microsporidiosis (*Microsporidia* Infection)
Myiasis
*Naegleria* Infection
Neurocysticercosis (Cysticercosis)
Neglected Tropical Diseases
Opisthorchiasis (*Opisthorchis* Infection)
Paragonimiasis (*Paragonimus* Infection)
*Pneumocystis jirovecii* Pneumonia
*Pseudoterranova* Infection (Anisakiasis, *Anisakis* Infection)
Sappinia
Scabies
Soil-transmitted Helminths
Strongyloidiasis (*Strongyloides* Infection)
Swimmer's Itch (Cercarial Dermatitis)
Taeniasis (*Taenia* Infection, Tapeworm Infection)
Toxoplasmosis (*Toxoplasma* Infection)
Waterborne Diseases
Zoonotic Diseases (Diseases spread from animals to people)

In many instances, the compositions according to the present invention may be formulated as solutions for application to a surface or for introduction into a water supply or a swimming pool. In certain embodiments according to the present invention, the composition takes the form of a cream or lotion to be applied to the skin or other surface. In such instances, an emulsion is used to formulate the composition. The term "emulsion", "oil-in-water emulsion" and "water-in-oil emulsion" are used synonymously throughout the specification to describe certain embodiments of compositions according to the present invention. An "emulsion" according to the present invention is a cream or lotion which is generally formed by the suspension of a very finely divided liquid, in this case water, in another liquid, in this case, an oil, or alternatively, an oil, in water. In the present invention, an emulsion is formed when the water phase is compatibilized in an oil phase, such that the water phase becomes dispersed within the oil phase, generally by inclusion of a surfactant or emulsifier. In certain embodiments according to the present invention, the composition takes the form of a powder, tablet or pill that will be added to an aqueous and then utilized for a specific use application. In yet other embodiments the compositions may be orally ingested when configured as a capsule, tablet or powder. In another embodiment the composition may be infused subgingivally as a liquid, gel or other medium as a periodontal treatment.

The term "oil" is used throughout the specification to describe any of various lubricious, hydrophobic substances obtained from animal, vegetable and mineral matter which are used in compositions according to the present invention. Oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity.

Additional oils for use in the present invention may include, for example, mono-, di- and tri-glycerides which may be natural or synthetic (derived from esterification of glycerol and at least one organic acid, saturated or unsaturated, such as for example, such as acetic, propionic, butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

Preferred oils for use in the present invention include petrolatum, mineral oil or mixtures of petrolatum and mineral oil where the amount of petrolatum to mineral oil (on a weight/weight basis) ranges from about 1:20 to about 10:1, preferably about 1:5 to about 5:1, more preferably about 1:3 to about 1:1, depending upon the end use of the emulsion composition. The inclusion of petrolatum and/or mineral oil and/or the ratio of petrolatum to mineral oil in the present compositions will greatly influence the final viscosity of the water-in-oil compositions according to the present invention and generally, are rather inert to the components which are otherwise included in compositions according to the present invention. Emulsions according to the present invention comprise water in an amount ranging from about 25% to about 90%, about 35% to about 85%, about 40% to about 80%, about 45% to about 75% by weight and an oil in an amount ranging from about 5% to about 65%, about 10% to about 50%, about 15% to about 50% and an emulsifier ranging from about 1% to about 15%, about 2% to about 10%. In addition to the above components, additional components may be added to the emulsion including fragrances, emollients, solvents/diluents, additional antimicrobial agents, pigments, foaming agents, gelling agents, solubilizing agents, humectants, stiffening agents and mixtures of these components, among numerous other components.

The term "surfactant" is used to describe compositions according to the present invention which are included in certain disinfectant compositions according to the present invention for their ability to solubilize and remove oils and other materials from a surface exposed to the present compositions. Preferred surfactants for use in the present invention are those surfactants which may produce foams (but are not required to) upon exposure to a surface. Exemplary surfactants for use in the present invention include nonionic, anionic, cationic, amphoteric and zwitterionic surfactants. Preferred anionic surfactants for use in the present invention include, for example, alkyl sulfates, alkylether sulfates, alkyl benzene sulfonates, alpha olefin sulfonates, N-alkyl sarcosinates, alkyl sulfosuccinates, alkyl phosphates, alkylether phosphates and alkyl or alkylether carboxylic acid salts, among others.

The term "additional compatible germicide" or "additional germicide" is used to describe compatible germicidal agents which may be further included in compositions according to the present invention to enhance the disinfectant/germicidal/antimicrobial activity of compositions according to the present invention. Additional germicidal agents which may be included in compositions according to the present invention include, for example, numerous peroxygen compounds such as peracetic acid, perborate, peroxides, including hydrogen peroxide and benzoylperoxide, among others, along with alcohols such as ethanol, isopropanol, propanol and saturated octanoic acid. In certain embodiments, caprylic acid may also be included in compositions according to the present invention. The additional germicides are added to the present compositions to enhance the disinfectant/germicidal properties of the present compositions and often synergistically enhance the germicidal activity of compositions according to the present invention.

The term "thickening agent", "gelling agent" or "thickener" is used to describe a component which may be included in compositions according to the present invention to increase the viscosity of the composition to make the composition more readily adhere to a surface, especially a ceiling, a vertical surface or a surface which is present on an incline. Gelling agents for use in the present invention include standard gelling agents which are stable to acid solutions and which limit degradation due to oxidation.

Additional components which can be added to compositions according to the present invention include components selected from non-aqueous solvents (ethanol, isopropanol, n-propanol, etc. which also may be included as a secondary germicide), surfactants, emulsifiers, including secondary emulsifiers, emollients, oils, humectants, oils (polar and non-polar), conditioning agents, thickeners/thickening agents (including gelling agents), medicaments, fragrances, preservatives, skin protecting agents, pigments, dyes, coloring agents and mixtures thereof in order to provide compositions exhibiting characteristics consistent with the use of the compositions, depending upon the surface to be treated, which surfaces include biological surfaces especially including keratinous or mucosal tissue of an animal, including a human.

DETAILED DESCRIPTION OF THE PREFERRED EMBODIMENTS

The present invention is further described and embellished through the presentation of the following examples. Accordingly, additional understanding of the present invention, including particular aspects and embodiments, as well as their utility and advantages, will be apparent by referring to the detailed description below. The below described examples should not be taken to limit the breadth and application of the present invention in any way.

The different biocidal properties of complexed versus uncomplexed molecular iodine are well known to one skilled in the art. Gottardi demonstrated that the instability of molecular iodine in an aqueous environment is due to a complex equilibria established after hydration of molecular iodine; more than 6 different iodine species are formed including iodate (Gottardi, W., *Iodine and Iodine Compounds*, in *Disinfection, Sterilization, and Preservation*, S. S. Block, Editor. 1991. p. 152-166). Stable aqueous disinfectants based on complexing molecular iodine were developed in the 1800s and theses formulations rely upon high concentrations of iodide that serve to complex molecular iodine, e.g. Lugol's solution. Polyvinylpyrrolidone replaced iodide as the primary complexing agent in iodine-based germicides in the 1950s.

Complexed molecular iodine per se is not biocidal in contrast to uncomplexed molecular iodine. This stark distinction in biocidal activity led to an outbreak of bacterial infections from a batch of 10% PVP-I that harbored viable bacteria (Favero, M. S., *Iodine-champagne in a tin cup*. Infect Control, 1982. 3 (1): p. 30-32). Formulations based on complexed iodine are commonly referred to as iodophors and all of these compositions contain the vast majority of iodine species in a form that do not contribute biocidal activity. In fact, it has been clearly demonstrated that the biocidal efficacy of an iodine-based germicide is directly proportional to the concentration of uncomplexed molecular iodine. (Gottardi, W., Zentralbl Bakteriol [B], 1980. 170(5-6): p. 422-30).

The present application teaches compositions and methods that provide uncomplexed formulations of molecular iodine that are stable and capable of being placed into commercial distribution channels. The compositions described in this application can be formulated to provide the optimal concentration for a particular use indication in contrast to iodophor compositions where the concentration of molecular iodine is determined by the iodophor equilibrium that provides adequate stability for molecular iodine. The compositions anticipated in this application: (a) provide a constant thiosulfate titratable level of iodine over the shelf-life of the product and (b) exhibit a chemical activity of molecular iodine that is equal to at least about 50% (often at least about 60%) of a pure composition of an equivalent concentration of molecular iodine (i.e. equivalent in terms of total iodine) in a 0.1N HCl solution as measured by the potentiometric method of Gottardi. The compositions described in this application also provide the ability to incorporate other compatible biocides to enhance the use properties of molecular iodine; for example, additional biocides can be selected to complement the spectrum of activity or the rate of biocidal activity. The potential benefits of this formulation approach include: use of less iodine with an associated reduction in environmental burden; lower cost; the ability to provide targeted levels of molecular iodine that are appropriate to different use applications; the ability to incorporate additional biocidal agents; and a reduced potential for negative organoleptic or material incompatibilities.

The compositions and methods taught here include products that are sold ready to use and those products which are admixed or diluted by the end user prior to use. The dosage forms contemplated in this application include, but are not limited to, solids, pastes, sprays, aerosols, foams, gels, lotions, creams, ointments and liquids. The germicides may be applied directly to surfaces. Other methods of application include, but are not limited to wipes, rinses, drops, gargles, sprays, hose, dips, towel/towelette, cloth, lavage, injection, irrigation, dip, immersion, sponge, mop, vapor or mist. In preferred aspects of the invention, the ready-to-use compositions and methods taught herein provide an activated use-life of at least 1 month and preferably between 6 months and 2 years or even longer (up to about 5 years). During the activated use-life of the compositions anticipated in this application, the thiosulfate titratable iodine does not decrease substantially below the initial concentration and the compositions maintain activity (i.e. they do not become inactive). Maintenance of a minimum concentration for thiosulfate titratable iodine is achieved using three principal formulation strategies: (1) the omission of complexing agents that lower the chemical activity of molecular iodine and (2) incorporation of a molar excess of iodate that provides at least a 10% molar excess of iodate to molecular iodine and as much as a twenty-five-fold molar excess of iodate to molecular iodine and (3) omission of any additive that consumes or causes the reduction of molecular iodine to a measurable degree or that negatively impacts activity.

It is well known to one skilled in the art that the spectrum of activity and speed of kill for different germicidal agents varies. There is a potential benefit of being able to incorporate more than one germicide into a germicidal composition depending upon which pathogens are of interest. The compositions contemplated in this application are compatible with different germicides provided the additional germicides (1) do not complex molecular iodine (2) do not react with molecular iodine (3) are active at an acid pH and (4) do not reduce the activated use-life of molecular iodine. Representative additional germicides compatible with the formulations contemplated in this application include: hydrogen peroxide; peracetic acid; ethanol; 1-propanol; 2-propanol; and saturated octanoic acid.

The compositions contemplated in this application are suitable for use over a temperature range of from below 0 degrees to 58 degrees centigrade. The biocidal activity of uncomplexed molecular iodine is more rapid than a comparable concentration of complexed molecular iodine since iodophor compositions lose biocidal activity at low temperatures since the rate at which complexed molecular iodine dissociates from an iodophor limits the availability of the biocidal form of (molecular iodine).

The pH range for the formulations in this application is between 1.5 and 6.5, often 2.0 and 5.5 with a preferred pH range of about 2.0-3.0 to 5.0. Commonly used weak organic acids are suitable buffering agents for the compositions contemplated in this application including citric acid, lactic acid, acetic acid and formic acid, among others disclosed herein; other commonly used buffering agents such as the sodium phosphates are also compatible with the compositions contemplated in this application.

It is understood that various inert ingredients or additives will be added to the compositions contemplated in this application including agents that mask odors, increase solubility for actives or inerts, lower liquid-to-liquid or liquid-to-solid interfacial tension, control foaming, increase viscosity, provide detergency or soil release, chelate, act as a dispersant, lower the vapor pressure of molecular iodine by means other than complexation, reduce scaling, prevent flocculation and emulsify. In general, for an additive to be compatible with the formulations contemplated in this application said additive should (a) not lower the chemical activity (as measured potentiometrically) of molecular iodine by more than 5% at the intended use concentrations, (b) not affect the stability of molecular iodine as measured by sodium thiosulfate titration when the test article is stored at 37 degrees centigrade for 6 weeks and (c) not cause the base composition to form a color or present an otherwise unattractive appearance. It is understood that additives that lower the vapor pressure of molecular iodine by means other than complexation can lower the chemical activity of molecular iodine which is acceptable provided the thiosulfate titratable iodine level is not altered and there is no increase in the formation of triiodide. For instance, commonly used surfactants that are compatible with the formulations contemplated in this application include $C_{10-16}$ sodium dodecyl benzene sulfonic acid, linear alkylbenzene-sulfonates, Dowfax akylphenol ethoxylates, gluconamides, nonylphenoxypolyethyleneoxy ethanol sulfate, Ecosurf EH3, Ecosurf EH6, Ecosurf EH9, nonanoic acid 2,3-dihydroxypropyl ester, dodecanoic acid 2,3-dihydroxypropyl ester and capryllic acid and as otherwise described herein.

Applications of the Present Invention

The present invention may be used in the following applications or general uses, among others without limitation as disinfectants, sanitizers, antimicrobial agents and/or biocides:
Low level hard surface disinfectants
Intermediate level hard surface disinfectants
Hospital grade hard surface disinfectant
Sporicides for hard surfaces or medical/dental equipment and instruments
High level disinfectant
Liquid chemical sterilant
Hand sanitizer
Hand wash
Hand rub
Food contact surface sanitizer
Dairy sanitizer
Prevention of food spoilage
Extension of shelf-life for fruits, vegetables, meats, dairy, seafood and grains
Carcass wash
Poultry dip
Flower vase life extender
Food spoilage retardant
Food sanitizer
Dish and utensil sanitizer (manual and automatic)
Fruit and vegetable cleaner and sanitizer
Meat sanitizer
Fish sanitizer
Grain sanitizer
Vegetable sanitizer
Fruit sanitizer
Water disinfection
Pool disinfection
Aquaculture
Animal husbandry
Agriculture
Oil field biofilm remediation
Seafood processing
Dairy production
Breweries
Meat packing
Pre-procedural rinse (dental office)
Mouthwash
Intra-oral irrigation (for use with oral irrigators such as Water Pik)
Sub-gingival irrigation or infusion (dental office professional use)
Biofilm remediation
Hand scrub (surgical pre-operative)
Antiseptic Pre-operative patient surgical antiseptic
Ear drops or ear rinse
Eye drops
Contact lens solution
Throat gargle
Throat spray
Oral ingestion for gastrointestinal diseases
Oral ingestion
Wound disinfection
Dialysis equipment disinfection
Vaginal douche
Iodine impregnated medical devices (e.g. catheters and ports)
Iodine impregnated face masks
Iodine impregnated tampons
Iodine impregnated dental floss
Iodine impregnated wound dressings and band-aids
Sinus spray (or rinse)
Nasal spray (or rinse)
Iodine impregnated chewing gum
Iodine impregnated mouth melts
Iodine impregnated lozenges
Iodine toothpaste
Inhalation mist
Inhalers
Vaporizers
Urinary bladder lavage
Abdominal or thoracic cavity lavage
Skin and scalp treatment
Athlete's foot soak
Eyewash
Teat dip
Vaginal cream
Ophthalmic ointment
Colonic irrigation
Environmental mold remediation
Humidifiers
Air conditioning systems
Dental infections
Tissue and organ transplants and grafts
Iodine releasing implants
Disinfecting dental cavity preparations (prior to restoration)
Root canal sealer and irrigant
Egg disinfection
Fish roe disinfection
Condom iodinated lubricant
Oral ingestion for fibrocystic breast disease
Commercial and home dishwashers
Surgical wound closure
Iodine releasing soaps
Government and military use (combating bioterrorism)
Veterinary use
Horticulture
Tattoo parlors
Food handlers
Herpes infections
Periodontal rinse
Trans-tympatic (ear drum) injections for otitis media
Iodine releasing drains
Burn spray
Iodine releasing ear drains (tubes)
Iodine releasing periodontal (subgingival) bioresorbable polymer
Blood dialysis
Iodine impregnated tissues (Kleenex)
Iodine tablets for systemic viral infections
Iodine rectal wipes
Iodine releasing anti-inflammatory (steroidal) ointments and creams
Iodine releasing underarm spray or roll-on deodorants
Iodine impregnated dental fillings
Shampoos
Dental dry socket treatment
Pericoronitis
Female breast nipple infections
Skin graft infections
Dental laboratories
Combined with monoclonal antibodies for viral targeting
Cold and Flu preventive
Dental water lines (biofilm preventive)
Oral Mucositis

EXAMPLES

Example 1

The following experiment was performed to demonstrate that a composition of molecular iodine prepared using a molar ratio of iodide to iodate of 5 is not stable in an aqueous environment in the absence of sequestering/binding agents like polyvinylpyrrolidone. The following materials were used for this example: sodium iodide (Acros Organics, Cat. 203182500; Lot A03011333); sodium iodate (Acros Organics, Cat. 201765000 Lot A0322553); sodium carbonate (Fisher Scientific, Cat. S252-3; Lot3AA12080311A) and citric acid (Fisher Scientific, Cat. A940-500; Lot 252559).

Control solutions of molecular iodine were prepared in glass 1 liter Teflon-lined screw top bottles. All control solutions contained the following: 0.106 grams of sodium carbonate and 7.5 grams of citric acid. All control solutions were prepared by using a molar ratio of iodide to iodate of 5.0. The concentration of iodide/iodate added to each control solution varied depending upon the desired final concentration of molecular iodine. The final concentrations of molecular iodine prepared in the stock solutions were: 25 ppm (24.5 mg NaI/6.5 mg NaIO$_3$), 50 ppm (49 mg NaI/13.3 mg NaIO$_3$), 75 ppm (74 mg NaI/19.6 mg NaIO$_3$), 100 ppm (99 mg NaI/26.2 mg NaIO$_3$), 150 ppm (148 mg NaI/39.2 mg NaIO$_3$) and 250 ppm (208 mg NaI/66.3 mg NaIO$_3$).

Aliquots of 100 mL were transferred into ten different 150 mL Teflon-lined screw top bottles The bottles were stored at 30 degrees C. in a laboratory in Boynton Beach, Fla. during the summer of 2013. The following analytical measurements were made on the samples: (1) USP thiosulfate titrations and (2) direct potentiometric measurement of molecular iodine.

All free molecular iodine values cited in this example and the other examples contained in this application, were determined according to the potentiometric method (W. Gottardi, 1983, Fresenius Z. Anal Chem. 314:582-585). The advantage of the potentiometric method is that the concentration of free molecular iodine is determined directly in solution without subsequent manipulations, such as extraction or equilibrium dialysis; this provides a more accurate measurement. A Fisher reference electrode (Fisher Scientific Company, LLC, Pittsburgh, Pa.; Fisher Catalog No. 13-620-51) and platinum electrode (Fisher Scientific Company, LLC, Pittsburgh, Pa.; Fisher Catalog No. 13-620-115) were used with a Corning Model 345 pH meter (Nova Analytics Corp., Woburn, Mass.) to make the potentiometric measurements. A cylindrical screw top bottle lid with two holes drilled through the screw top lid was used to make potentiometric measurements. The diameter of one hole was sized to fit the iodide ion selective electrode; another hole was sized to fit the platinum electrode. The third hole was drilled to allow reagent to be added to or removed from the bottle via a syringe if required.

A standard stock solution of 0.1N sodium thiosulfate (Acros Organics, 1 N, Cat. No. 124270010) was diluted immediately prior to use and then used to titrate 1 mL of the test solution after the potentiometric measurement was completed. The initial concentrations of the stock solutions were confirmed with both potentiometric analysis and titration.

Thiosulfate titration was conducted as follows: (1) calculate how many μL of a 0.01N sodium thiosulfate was required to titrate 50% of the initial concentration; (2) add the entire volume of 0.01N sodium thiosulfate corresponding to 50% of the initial concentration of molecular iodine and observe if the solution reaches an endpoint; (3) if the sample remains clear for several seconds while stirring then the sample has lost at least 50% of the initial molecular iodine concentration; (4) if the sample remains blue then the sample is still considered to be stable.

Each day for 49 days a 10 mL sample was withdrawn from two samples of each concentration and titrated with thiosulfate as per the standard USP test. The results were averaged and plotted for each day. For each concentration the first measurement that demonstrated a 50% reduction in thiosulfate titratable iodine was identified. For the standard solutions with initial concentrations of molecular iodine of 100, 150 and 250 ppm a 50% loss was observed at day 21 to 24. For the standard solutions with initial concentrations of molecular iodine of 25, 50 and 75 ppm a 50% loss was observed at day 26 to 29. The concentration of molecular iodine was measured potentiometrically for each concentration on the first day that a sample demonstrated a minimum 50% reduction in thiosulfate titratable iodine. In each instance, the potentiometric measurement of free molecular iodine also demonstrated a minimum 50% loss in free molecular iodine.

Example 2

The activated use-life for commercial antimicrobial agents is an important product feature. Some products are stable once activated for years. A product that exhibits an abbreviated shelf-life is at a substantial commercial disadvantage. The primary active agent in all of the antimicrobial products contemplated in this application is molecular iodine. Prior examples demonstrate that molecular iodine is not stable in an aqueous environment.

It was noticed that a single composition in a series of formulations exhibited much greater stability than the others even though there was no chemical basis for this observation since all of the compositions under study were intended to contain a stoichiometric ratio of iodate to iodide. It was speculated that a weighing error may have led to this results. A simple DOE experiment was conducted to explore this observation wherein the weights of the different ingredients were varied higher and lower than the initially used concentrations. It was observed that those samples that received a higher concentration of iodate had enhanced stability. This experiment indicated that the cause of the initial anomalous result was a higher concentration of iodate. This suggested that it is possible to provide a stable minimum level of thiosulfate titratable iodine in uncomplexed molecular iodine formulations by incorporating iodate in molar excess to molecular iodine.

An experiment was then designed to explore the effect of a molar excess of iodate with respect to extending the aqueous stability of molecular iodine. As previously indicated, if the molar ratio of iodide to iodate of 5 to 1 is used there is a quantitative yield of molecular iodine. i.e. no molar excess. For this experiment the molar ratios of iodide to iodate in the test solutions were: 5.0, 3.32, 2.49, 1.99, 1.66, 1.24 and 1.0; these ratios represent the following relative molar excesses of iodate: to iodide 1.5, 2, 2.5, 3, 4 and 5 fold.

A series of compositions with different iodide to iodate ratios were prepared as described in experiment 1 using glass 1 liter Teflon-lined screw top bottles. All of these test solutions initially provided 300 ppm of molecular iodine. All solutions contained a 7.5 grams of citric acid. The concentrations of sodium iodate and sodium iodide are shown below in Table 1. The solutions were prepared by dissolving the citric acid in 900 mL of distilled water, then under stirring until a clear solution was formed. Sodium iodide was completely dissolved and then the sodium iodate was added under stirring with the lid on the bottle sealed.

TABLE 1

| Iodate to Iodide Molar Excess | | | |
|---|---|---|---|
| Molar Excess of Iodate | NaI/IO3 Ratio | Molarity NaI | Molarity Iodate |
| — | 5.0 | 0.00197 | 0.000394 |
| 1.5 | 3.3 | 0.00197 | 0.000591 |
| 2 | 2.5 | 0.00197 | 0.000788 |
| 2.5 | 2.0 | 0.00197 | 0.000985 |
| 3 | 1.7 | 0.00197 | 0.001182 |
| 4 | 1.2 | 0.00197 | 0.001576 |
| 5 | 1.0 | 0.00197 | 0.00197 |

For each formulation, aliquots of 100 mL were transferred into ten different 100 mL Teflon-lined screw top bottles. The bottles were stored in at an average temperature of 30 degrees C. in a laboratory in Boynton Beach, Fla. starting in May of 2013. Every week, a one mL sample was withdrawn from one of the 100 mL bottles and for each of the different iodide/iodate ratios a USP thiosulfate titration was performed. A single transfer of 0.01N sodium thiosulfate which neutralized 240 ppm molecular iodine was added to test solutions. A potentiometric measurement of molecular iodine was made at the first time point that reached an endpoint by the single thiosulfate addition.

The control solution which had a molar ratio of 5/1 of iodide to iodate demonstrated a minimum 20% or greater loss at day 14. The potentiometric measurement of the control solution indicated a molar ratio of molecular iodine to thiosulfate titratable iodine of 73.4%. In contrast the sample with a molar excess of 1.5 of iodate to iodine did not exhibit loss of thiosulfate titratable iodine over the first 11 weeks. At week 11 the molar ratio of molecular iodine to thiosulfate titratable iodine was 76.1%. All test solutions with a molar excess of iodate of 2 or more beyond the stoichiometric amount did not demonstrate a loss of molecular iodine for 6 months at which point the experiment was terminated. This study demonstrates that a molar excess of iodate to iodide can maintain the concentration of molecular iodine for an extended period of time.

Example 3

A variation of the experiment described previously was performed. Instead of using iodide, molecular iodine was weighed and added directly to the formulation. After the molecular iodine was dissolved, a molar excess of iodate to molecular iodine was established by adding sodium iodate at a molar ratio of 1.5, 2.0, 2.5, 3.0, 4.0 and 5.0. The control for this experiment did not contain any iodate. The stability of molecular iodine was evaluated over time using thiosulfate titration. The thiosulfate titration was conducted as follows: (1) add a volume of 0.01N sodium thiosulfate which neutralized 75% of the initial concentration of molecular iodine and observe if the solution reaches a transient endpoint; 9(2) if the sample clears for a second or two then the sample has lost at least 25% of the initial molecular iodine concentration; (4) if the sample remains blue then the sample is still considered to be stable.

The following materials were used for this example: molecular iodine crystals (Puritan Products, Bethlehem, Pa.; ACS Reagent Grade, Lot 069106); sodium iodate (Acros Organics, Cat. 201765000, Lot A0322553); and citric acid (Fisher Scientific, Cat. A940-500; Lot 252559).

All solutions were prepared by adding 7.5 grams of citric acid to 900 mL of distilled water in a volumetric beaker and the citric acid was dissolved under stirring. Then, in each solution 0.300 grams of molecular iodine was added as crystals and a glass stopper was placed in the mouth of the volumetric to prevent evaporation; water was added to reach 1 liter and then the molecular iodine was stirred until it dissolved. This solution served as the stock solution for the experiment.

Varying amounts of sodium iodate were added to 100 mL aliquots of the stock solution in Teflon-lined screw top bottles. The control sample did not receive any iodide. The number of milligrams of sodium iodate added to the different experimental samples (100 mL each) was 35.1, 46.7, 58.4, 70.1, 93.6 and 117. The iodate was dissolved after screwing the lids tightly shut and placing the bottles on a rocker. The bottles were stored in a laboratory at 30 degrees C. in Boynton Beach, Fla. during the summer of 2013. The stability of all of the different samples was followed weekly by USP thiosulfate titrations as described above.

Each week a one mL sample was withdrawn from each of the test solutions and the control solution and titrated with thiosulfate as described above. Any solution that demonstrated a 50% reduction in thiosulfate titratable iodine was considered to have been unstable. For the standard solution a 25% loss was observed at the end of the $3^{rd}$ week. The sample with a molar excess of iodate to molecular iodine of 1.5 did not demonstrate a 25% loss until the $12^{th}$ week. All other samples had not demonstrated a 25% loss at week 16 which is when the experiment was ended.

Example 4

A further objective was to combine molecular iodine with other agents to demonstrate compatibility of multiple microbicides contemplated in this application. Enhanced microbicidal activity may be obtained by combining different chemical agents of known germicidal activity in the same formulation. A 300 ppm molecular iodine composition prepared by reacting iodide and iodate at a 5/1 molar ratio in an acidic solution with a molar excess of iodate to molecular iodine of 2; this composition (the base composition) was used to determine if other known biocidal agents would be compatible with this formulation approach.

To determine if a biocide was compatible, the biocide was added at increasing concentrations to the base solution. If the solution became deeply colored the additive was deemed to be incompatible. If the amount of thiosulfate titratable iodine decreased, the solution was deemed to be incompatible since this indicated that the molecular iodine reacted with the added biocide or that iodine precipitated due to the biocide's interference or interaction with iodine I The following biocides were tested: phenol/phenate; phenolics; orthophenylphenol; benzyl-4-chlorophenol; ethanol; 1-propanol; iso-propanol; parachlorometaxylenol; hydrogen peroxide; sodium dichloro-s-triazinetrione; amylphenol; phenylphenol; di-isobutyl-phenoxy-ethoxyethyl dimethyl benzyl ammonium chloride; alkyl dimethyl benzyl ammonium chloride; alkyl dimethyl ethylbenzyl ammonium chloride; benzyl-4-chlorophenol; 1-octanaminium-N,N-dimethyl-N-octyl-chloride; octanoic acid; diethyl toluamide; N,N"-bis(4-chlorophenyl)-3,12-diimino-2,4,11,13-tetraazatetradecanediimidamide (2:1); 4-chloro-3,5-xylenol; sodium dichloro-s-acid; and peracetic acid.

Most of the additional biocides were not compatible with molecular iodine. The addition of most of the phenolics generated increasingly colored solutions and also reduced titratable iodine. The quaternary ammonium compounds generally reduced thiosulfate titratable iodine and some also caused the solution to become colored. Several of the potential biocides did not reduce thiosulfate titratable iodine for the duration of this experiment which was 6 weeks. These included: hydrogen peroxide (3 to 12%); peracetic acid (25 to 50,000 ppm); ethanol (10-95%); 1-propanol (10-95%); 2-propanol (10-95%); and octanoic acid (saturated).

Example 5

A further objective of this invention was to incorporate surface active agents in the compositions contemplated in this application to enhance the cleaning and wetting properties of said compositions. A series of surface active agents were screened to insure their compatibility with the molecular iodine based composition contemplated in this application. A 985 micromolar concentration of molecular iodine was prepared by dissolving elemental iodine crystals in a sealed glass volumetric flask containing the base composition.

The base aqueous composition contained 2.0% n-propanol, 3000 ppm peracetic acid, 4.95% hydrogen peroxide, 1.97 millimolar sodium iodate and 0.5% citric acid. Samples of the following surface active agents or classes of surface active agents were obtained from various manufacturers and evaluated for compatibility with molecular iodine. For a surface active agent to be compatible it had to (a) not lower the activity (as measured potentiometrically) of molecular iodine by more than 5% at the lower and upper suggested use concentrations for said surface active agent, (b) not affect the stability of molecular iodine as measured by sodium thiosulfate titration when the test article was stored at 37 degrees centigrade for 6 weeks and (c) not cause the base composition with said surface active agent to form a deep color or otherwise unattractive appearance when the surface active agent was added at increasing concentrations.

The following classes (or specific compounds) of surface agent agents were tested: $C_{10-16}$ sodium dodecyl benzene sulfonic acid, linear alkylbenzenesulfonates, lignin sulfonates, fatty alcohol ethoxylates, $C_{12-13}$ ethoxylated propoxylated alcohols, polyethoxylated polyoxypropylenes, alkylphenol ethoxylates, gluconamides, glyceramides (loss of activity), glyceroglycolipids, nonylphenoxypolyethyleneoxy ethanol sulfate, Dowfax, Ecosurf EH3, Ecosurf EH6, Ecosurf EH9, nonanoic acid 2,3-dihydroxypropyl ester, dodecanoic acid 2,3-dihydroxypropyl ester, capryllic acid and polyvinylpyrrolidone.

Lignin sulfonates, glyceramides (loss of activity), glyceroglycolipids and polyvinylpyrrolidone exhibited negative properties for the formulations anticipated by this application. These surfactants either (a) reduced thiosulfate titratable within 24 hours at room temperature; (b) immediately reduced the chemical activity of molecular iodine by more than 10%; or (c) produced a darkly colored solution.

$C_{10-16}$ sodium dodecyl benzene sulfonic acid, linear alkylbenzenesulfonates and Dowfax were compatible with the compositions contemplated under this application provided the concentration used of these surface active agents was less than 1.5% (w/w) of the final composition. Akylphenol ethoxylates, gluconamides, nonylphenoxypolyethyleneoxy ethanol sulfate, Ecosurf EH3, Ecosurf EH6, Ecosurf EH9, nonanoic acid 2,3-dihydroxypropyl ester, dodecanoic acid 2,3-dihydroxypropyl esterand capryllic acid were compatible at all concentrations tested.

Microbiological tests (study #130621-204) were initiated on Jul. 2, 2013 and completed on Jul. 16, 2013 at BioScience Laboratories located at 1765 S. 19th Avenue Bozeman, Mont. 59718. The test article was evaluated in a spray application versus glass slide carriers contaminated with *Klebsiella pneumoniae* (ATCC #4352), *Staphylococcus aureus* (ATCC #6538), and *Trichophyton mentagrophytes* (ATCC #9533). The test article contained 200 ppm of molecular iodine, 3% hydrogen peroxide, 0.2% citric acid, 112 mg. monolaurin, 20 ml ethanol, and a molar excess of iodate to molecular iodine of 2.0.

An initial suspension of each challenge species containing approximately $10^8$ CFU/mL was prepared; Fetal Bovine Serum was added to each suspension to produce final challenge suspensions containing a 5% (v/v) soil load. A total of 11 glass slide carriers (microscope slides) were contaminated with a 0.01 mL aliquot of each challenge suspension and dried at 35° C. for approximately 35 minutes. Each dried contaminated carrier was treated with the test solution: the spray bottle containing the test solution was maintained at a 45° angle and sprayed onto each contaminated carrier until the carrier was completely wet.

Each carrier was maintained in a horizontal position and exposed for either 30 seconds, 1 minute, or 2 minutes (timing of the exposure commenced upon completion of the spray application). Following the selected exposure time, 10 carriers per challenge species were subcultured in separate tubes containing a 40 mL neutralizing broth and incubated. Following incubation, the tubes were examined for the presence of growth, and results were reported as "Growth (+)," or "No Growth (−)."

One carrier per challenge species per exposure time was evaluated for viable microbial counts, post-treatment: the treated carrier was transferred to a tube containing neutralizing solution, and aliquots were diluted and plated, in duplicate. The plates prepared were incubated in a manner appropriate for each specific test organism; following incubation, the colonies on the plates were enumerated, and the viable CFU/carrier was determined.

In addition to the testing of microorganisms which are presented in Tables 2 and 3, additional testing of microbes (bacteria or fungus) were also performed. For the primary bacteria, sixty inoculated carriers (stainless penicylinders) are inoculated with the bacteria and dried. The dried cylinders are then sequentially immersed into 10 ml. of the disinfectant and exposed to the disinfectant for a predetermined length of time. The carriers are transferred to a culture media to neutralize the disinfectant. The carriers are incubated and examined for the presence or absence of growth. Other than the primary three bacteria (Tables 2 and 3 hereof), all of the other bacteria are tested on 10 carriers.

In the fungicidal test (*Trichophyton*), the disinfectant is inoculated with the fungi in suspension. Exposure is for 5, 10 and 15 minutes. The fungi is removed and neutralized. The cultures are incubated for the presence or absence of growth. No growth must be observed after 10 minutes of exposure to disinfectant.

In the viral test, the following protocol was used. AOAC use dilution test was modified for virus testing as follows: one surface for each of two samples, representing two different batches of disinfectant, is tested against a recoverable virus endpoint titer of at least 10 viable viral particles from the test surface for the exposure period specified on the label at less than or equal to ten minutes.

The results are presented in tables 2-9. In general, the compositions were essentially effective in eliminating/disinfecting bacteria, spores, fungi and viral titer as set forth in the attached tables. The following observations were made for the particular microbes:

*Acinetobacter baumannii*. This is a serious hospital based infection of the infirmed Tested by use dilution method (EPA method for multi-use products) must have 0/10 failures to make label claim. The present invention passed in 30 sec. Most prior art compositions take minutes.

*Candida albicans*. This is a serious yeast infection. The present invention evidenced 0/10 failures with 30 sec. exposure. Most prior art compositions take minutes and are less effective.

*Klebsiella pneumoniae*. This is a highly pathogenic bacterium. It is causative for pneumonia. Again, the present invention evidenced 0/10 failures, with a 30 second kill time. Most prior art products take minutes and are less effective.

*Tricophyton mentagrophytes*. This is the causative agent for athletes foot fungus. Test results complied with EPA criteria and showed 0/10 failures with a 30 second kill time. Most products require 5-10 minutes.

*Pseudomonas aeruginosa*. This is a problematic hospital infection. EPA requires effective disinfection of this organism to qualify as hospital strength. EPA testing allows up to 6 failures out of 60 in 10 minutes The present compositions passed the EPA test with 1 failure in 45 seconds.

*Salmonella enterica*. Same EPA requirements as for Psudeomonas. The present compositions showed only 1 failure out of 60 in 45 seconds, easily surpassing EPA testing criteria of an allowable 10 minutes.

*Staph aureus*. Another bacteria required by the EPA to establish a composition as a hospital grade disinfectant. The EPA allows 3 failures in ten minutes; the present composition showed no failures in 30 seconds.

Hepatitis A virus. This is a non-enveloped virus, very difficult to kill. Most products aren't effective against this virus. The present compositions totally inactivated this virus in 15 seconds and achieved a 4 log kill (compared to 10 minutes allowed by EPA).

Polio virus. This virus is considered the benchmark for virus killing ability. Generally, if you kill polio, you can kill any virus. The present composition totally inactivated this virus in 90 seconds with a 4 log kill. This kill-time was significantly shorter than the 10 minutes allowed by the EPA.

Norovirus (murine surrogate). The present compositions showed a complete inactivation of this virus in 30 seconds with a 4 log kill. The allowable EPA kill-time is ten minutes. The results are gleaned from the tables which follow.

TABLE 2

Qualitative Carrier Evaluation - Results
Test Formulation prepared with hard water

| Challenge | Exposur | Challenge Suspension Initial | Baseline Carrier Recovery (CFU/untreated | Number of Positive Carriers per Number |
|---|---|---|---|---|
| Klebsiella pneumoniae (ATCC #4352) | 30 seconds 1 minute | $3.35 \times 10^8$ | $2.78 \times 10^3$ | 0/10 1/10 |
| Staphylococcus aureus (ATCC | 30 seconds 1 minute 2 minutes | $6.65 \times 10^8$ | $4.42 \times 10^6$ | 5/10 1/10 0/10 |
| Trichophyton mentagrophytes (ATCC | 30 seconds 1 minute 2 minutes | $1.87 \times 10^7$ | $8.60 \times 10^2$ | 0/10 0/10 0/10 |

[1]Prepared with 5% (v/v) added soil load.

TABLE 3

Quantitative Carrier Evaluation - Results

| Challenge Microorganism[1] | Exposure | Challenge Suspension Initial Population | Baseline Carrier Recovery (CFU/untreated carrier Post- | Post-Exposure Carrier Recovery |
|---|---|---|---|---|
| Klebsiella pneumoniae (ATCC #4352) | 30 seconds 1 minute | $3.35 \times 10^8$ | $2.78 \times 10^3$ | $<4.00 \times 10^1$ $<4.00 \times 10^1$ |
| Staphylococcus aureus (ATCC #6538) | 30 seconds 1 minute 2 minutes | $6.65 \times 10^8$ | $4.42 \times 10^6$ | $<4.00 \times 10^1$ $<4.00 \times 10^1$ $<4.00 \times 10^1$ |
| Trichophyton mentagrophytes (ATCC #9533) | 30 econds 1 minute 2 minutes | $1.87 \times 10^7$ | $8.60 \times 10^2$ | $<4.00 \times 10^1$ $<4.00 \times 10^1$ $<4.00 \times 10^1$ |

TABLE 4

Qualitative Carrier Evaluation - Results
Test Formulation H (see below)[b]

| Challenge Microorganism (ATCC #)[a] | Application | Exposure Time | Challenge Suspension Initial Population (CFU/mL) | Baseline Carrier Recovery[c] ($Log_{10}$ CFU/untreated carrier Post-drying) | Number of Positive Carriers Per Number Tested |
|---|---|---|---|---|---|
| Acinetobacter baumannii (ATCC #BAA-747) | Use-Dilution[d] | 30 seconds | $1.6550 \times 10^9$ | 6.3076 | 0/10 |
| Candida albicans (ATCC #10231) | Use-Dilution[d] | 30 seconds | $3.250 \times 10^8$ | 3.6766 | 0/10 |

[a]Prepared with 5% (v/v) added soil load
[b]Test formulation was prepared by mixing the following ingredients in sterile Water-for-Irrigation, USP, to produce 1 liter: 495 mL of 10% hydrogen peroxide, 7.5 grams citric acid, 0.112 grams fatty acid (dissolved in 20 mL 70% ethyl alcohol), 9 grams surfactant, 39 mL peracetic acid, and one Vial 2. One 2-liter batch of test formulation was prepared. Resulting formulation was applied via standard Use-Dilution Methodology.
[c]Three carriers evaluated: mean $log_{10}$ recovery reported.
[d]Reference AOAC 955.14.

TABLE 5

Norovirus type 1
Test Formulation #1
Virus: Marine Norovirus type 1
Host Cell Line: RAW Host Cell Line ATCC #TIB-7.1
Volume Plated per Well 1.0 mL

| Dilution ($-Log^{10}$) | Virus Control | Test 30 sec | Test 1 min | Test 2 min | Neutralization Control | Initial Population | Cytotoxicity Control | Cell Control (Negative Control) |
|---|---|---|---|---|---|---|---|---|
| −2 | NT | CT | CT | CT | NT | NT | ++++ | |
| −3 | ++++ | 0000 | 0000 | 0000 | ++++ | ++++ | 0000 | 0000 |

TABLE 5-continued

Norovirus type 1
Test Formulation #1
Virus: Marine Norovirus type 1
Host Cell Line: RAW Host Cell Line ATCC #TIB-7.1
Volume Plated per Well 1.0 mL

| Dilution ($-\text{Log}^{10}$) | Virus Control | Test 30 sec | Test 1 min | Test 2 min | Neutralization Control | Initial Population | Cytotoxicity Control | Cell Control (Negative Control) |
|---|---|---|---|---|---|---|---|---|
| −4 | ++++ | 0000 | 0000 | 0000 | ++++ | ++++ | 0000 | |
| −5 | ++++ | 0000 | 0000 | 0000 | ++++ | ++++ | NT | |
| −6 | ++++ | 0000 | 0000 | 0000 | ++++ | +++0 | NT | |
| −7 | 0000 | 0000 | 0000 | 0000 | 0000 | 0000 | NT | |
| $TCID_{50}$ ($\log_{10}$) | 6.50 | ≤2.50 | ≤2.50 | ≤2.50 | 6.50 | 6.25 | 2.50 | |
| $Log_{10}$ Reduction | N/A | ≥4.00 | ≥4.00 | ≥4.00 | | | | |
| Percent Reduction | | >99.99% | >99.99% | >99.99% | | | | |

+ CPE (cytopathic/cytotoxic effect) present
0 CPE (cytopathic/cytotoxic effect) not detected
NT Not Tested
N/A Not Applicable
CT Cytotoxicity Present
Note:
Data has not been QA reviewed

TABLE 6

Poliovirus
Test Formulation #1
Virus/Strain: Poliovirus/Chat (ATCC #VR-1562)
Host Cell Line: LLC-MK2 Host Cell Line ATCC #CCL-7.1
Volume Plated per Well 1.0 mL

| Dilution ($-\text{Log}^{10}$) | Virus Control | Test 30 sec | Test 1 min | Neutralization Control | Initial Population | Cytotoxicity Control | Cell Control (Negative Control) |
|---|---|---|---|---|---|---|---|
| −2 | NT | CT | CT | NT | NT | ++++ | 0000 |
| −3 | ++++ | 000+ | 0000 | NT | NT | 0000 | |
| −4 | ++++ | 0000 | 0000 | ++++ | ++++ | 0000 | |
| −5 | ++++ | 0000 | 0000 | ++++ | ++++ | NT | |
| −6 | ++++ | 0000 | 0000 | ++++ | ++++ | NT | |
| −7 | 0000 | 0000 | 0000 | 00++ | ++++ | NT | |
| −8 | 0000 | NT | NT | 0000 | 0000 | NT | |
| $TCID_{50}$ ($\log_{10}$) | 6.50 | 2.75 | 2.50 | 7.00 | 7.50 | 2.50 | |
| $Log_{10}$ Reduction | | 3.75 | 4.00 | | | | |
| Percent Reduction | | 99.98% | 99.99% | | | | |

+ CPE (cytopathic/cytotoxic effect) present
0 CPE (cytopathic/cytotoxic effect) not detected
NT Not Tested
N/A Not Applicable
Conclusion: Poliovirus was completely inactivated by the test product at 90 seconds; but not completely inactivated at 60 seconds.

TABLE 7

Hepatitis A
Test Formulation #1
Virus/Strain: Hepatitis A Virus (ATCC #VR-1402)
Host Cell Line: FRhK-4 Host Cell Line #CCL-1688
Volume Plated per Well 1.0 mL

| Dilution ($-\text{Log}^{10}$) | Virus Control | Test 15 sec | Test 30 sec | Neutralization Control | Initial Population | Cytotoxicity Control | Cell Control (Negative Control) |
|---|---|---|---|---|---|---|---|
| −2 | NT | CT | CT | NT | NT | ++++ | 0000 |
| −3 | NT | 0000 | 0000 | NT | NT | 0000 | |

TABLE 7-continued

Hepatitis A
Test Formulation #1
Virus/Strain: Hepatitis A Virus (ATCC #VR-1402)
Host Cell Line: FRhK-4 Host Cell Line #CCL-1688
Volume Plated per Well 1.0 mL

| Dilution ($-Log^{10}$) | Virus Control | Test 15 sec | Test 30 sec | Neutralization Control | Initial Population | Cytotoxicity Control | Cell Control (Negative Control) |
|---|---|---|---|---|---|---|---|
| −4 | ++++ | 0000 | 0000 | ++++ | ++++ | 0000 | |
| −5 | ++++ | 0000 | 0000 | ++++ | ++++ | NT | |
| −6 | ++++ | 0000 | 0000 | ++++ | ++++ | NT | |
| −7 | 0000 | 0000 | 0000 | 0+00 | ++0+ | NT | |
| −8 | 0000 | NT | NT | 0000 | 0000 | NT | |
| $TCID_{50}$ ($\log_{10}$) | 6.50 | 2.50 | 2.50 | 6.75 | 7.25 | 2.50 | |
| $Log_{10}$ Reduction | | 4.00 | 4.00 | | | | |
| Percent Reduction | | 99.99% | 99.99% | | | | |

+ CPE (cytopathic/cytotoxic effect) present
0 CPE (cytopathic/cytotoxic effect) not detected
NT Not Tested
N/A Not Applicable
A complete inactivation of the virus was shown in testing at 15 seconds and 30 seconds.

TABLE 8

*Staph. Aureus*
Qualitative Carrier Evaluation - Results
Test Formulation #1 (see below)[b]

| Challenge Microorganism (ATCC #)[a] | Application | Exposure Time | Challenge Suspension Initial Population (CFU/mL) | Baseline Carrier Recovery[c] ($Log10$ CFU.untreated carrier Post-drying) | Number of Positive Carriers per Number Tested |
|---|---|---|---|---|---|
| Staphylococcus aureus (ATCC #6538) | Use-Dilution[d] | 30 seconds | $4.95 \times 10^8$ | 6.2851 | 3/60 |
| | | 60 seconds | | | 0/60 |
| | | 90 seconds | | | 0/60 |

[a]Prepared with 5% (v/v) added soil load.
[b]Test Formulation was prepared by mixing the following ingredients in sterile Water-for-Irrigation, USP, to produce 1 liter: 495 mL of 10% hydrogen peroxide, 7.5 grams citric acid, 0.112 grams fatty acid (dissolved in 20 mL 70% ethyl alcohol), 9 grams surfactant, 39 mL peracetic acid, and on Vial 2, One 2-liter batch of test formulation was prepared. Resulting formulation was applied via standard Use-Dilution Methodology.
[c]Six carriers evaluated; mean $\log_{10}$ recovery reported
[d]Reference AOAC 955.15-Bacterial Use Dilution Method.

TABLE 9

*Pseudomas* and *Salmonella*
Qualitative Carrier Evaluation - Results
Test Formulation I (see below)[b]

| Challenge Microorganism (ATCC #)[a] | Application | Date of Evaluation | Exposure Time | Challenge Suspension Initial Population (CFU/mL) | Baseline Carrier Recovery[c] ($Log_{10}$ CFU/untreated carrier Post-drying) | Number of Positive Carriers Per Number Tested |
|---|---|---|---|---|---|---|
| seudomonas aeruginosa (ATCC #15442) | Use-Dilution | Jan. 17, 2014 | 45 seconds | $2.69 \times 10^9$ | 5.49 | 1/60 |
| | | Jan. 24, 2014 | 1 minute | $3.85 \times 10^9$ | 6.96 | 4/60 |

TABLE 9-continued

Pseudomas and Salmonella
Qualitative Carrier Evaluation - Results
Test Formulation I (see below)[b]

| Challenge Microorganism (ATCC #)[a] | Application | Date of Evaluation | Exposure Time | Challenge Suspension Initial Population (CFU/mL) | Baseline Carrier Recovery[c] ($Log_{10}$ CFU/untreated carrier Post-drying) | Number of Positive Carriers Per Number Tested |
|---|---|---|---|---|---|---|
| Salmonella enterica serovar Choleraesuis (ATCC #10708) | Use-Dilution | Jan. 17, 2014<br>Jan. 24, 2014 | 45 seconds<br>1 minute | $1.06 \times 10^{10}$<br>$1.17 \times 10^{10}$ | 6.01<br>7.92[d] | 0/60<br>3/60[d] |

[a]Prepared with 5% (v/v) added soil load
[b]Test formulation was prepared by mixing the following ingredients to produce a 1 liter batch: 737 mL peracetic acid (Peraclean 0.4%), 165 mL hydrogen peroxide (30%), one vial of each of sodium iodate and sodium iodide, one vial of fatty acid (dissolved in 20 mL ethyl alcohol), 7.5 grams citric acid, 9 grams surfactant, and 69 grams of sterile Water-for-Irrigation, USP. One 3-liter batch of formulation was prepared on each day of testing.
[c]Three carriers evaluated: mean $log_{10}$ recovery reported.
[d]Challenge species to be retested due to high baseline barrier recoveries.

Example 6—Corrosion

In this example, mild steel and aluminum were exposed to concentrations of peracetic acid (PAA) ranging from 25-2950 ppm for one week. In all cases, the steel either rusted completely or was severely blackened in one week at 88 deg. F. Aluminum became severely discolored but did not corrode. Acidified peroxide at 3 & 4.95% rusted steel. Brass became pitted with 500 ppm PAA. When steel and aluminum were exposed to a formulation, according to this invention, containing 25-2950 ppm PAA, no corrosion or discoloration was observed on steel after one week. Brass exposed for one week to the same composition resulted in no discoloration. In another composition according to the present invention with acidified peroxide plus $I_2$ on steel, no rust was evidenced.

Following the successful result for the present invention, the composition was modified such that three ingredients were systematically omitted from a formula (which contained peracetic acid as a base composition), leaving only one of the components in the composition. The three were EH-6, monolaurin and $H_2O_2$. These compositions were formulated with 500 ppm PAA in the formula, but iodine and acid were not present.

Variable Compositions and Results:

H2O2 only—no corrosion steel

EH-6 only (the preferred range of EH-6 in the formula is 0.25-2.0%, optimal range of 0.75-1.0%)—resulted in severe discoloration, but no rust Monolaurin only—severe discoloration, but no rust.

Monolaurin, H2O2 and EH removed-severe rust (these experiments run only on steel).

When mild steel is immersed in a solution of peracetic acid (any concentration ranging from about 25 to 5000 ppm), it begins to rust at room temperature in less than 30 minutes. In contrast the composition of the present invention with the identical concentration of peracetic acid, does not show any signs of corrosion, even after one week which is an unexpected result. Likewise, if you acidify hydrogen peroxide with citric acid, at the same levels used in the present invention, the steel sample will rust in hours or days. Moreover, citric acid itself will result steel without any other components.

Example 7 Food Preservation

An additional embodiment of this invention is the inhibition of deterioration or spoilage of foodstuffs. This experiment demonstrates that compositions of the invention can extend the useful life of various foods. The following materials were used for this example: sodium iodide (Acros Organics, Cat. 203182500; Lot A03011333); sodium iodate (Acros Organics, Cat. 201765000 Lot A0322553); sodium carbonate (Fisher Scientific, Cat. S252-3; Lot3AA12080311A) and citric acid (Fisher Scientific, Cat. A940-500; Lot 252559).

A solution of molecular iodine was prepared in a sterile glass 1 liter screw top bottle that contained 0.5 grams of sodium carbonate, 2.5 grams of citric acid, 24.5 mg of sodium iodide and 3.25 mg $NaIO_3$. The final concentration of molecular iodine was 25 ppm as determined by the direct potentiometric measurement of molecular iodine.

These experiments were intended to prove the hypothesis that compositions of the invention could extend the useful life of various foods. These are examples only and by no means limit the variety of foods or the extent to which spoilage is inhibited.

In the testing, the refrigerated shelf life of fruits and vegetables was significantly extended and mold formation was prevented compared to controls. Testing by an independent laboratory of a food-safe composition of the present invention confirmed its effectiveness against foodborne pathogens, destroying Listeria, E. coli, Salmonella and the Norovirus in 90 sec., achieving over 5 log kill (easily passing the EPA requirement for effectiveness as a food sanitizer). See below. This reduction in spoilage also extends to foods such as chicken and other meats and dairy products and grains among others. Independent laboratory testing of the present invention on chicken breasts confirmed significant pathogen reduction as well as an absence of sensory signs of spoilage.

In addition, testing with the present invention which contained iodine at lower concentrations (e.g. about 10-50 ppm, preferably about 20-30, often about 25 ppm) can be useful for treating viral and mucosal infections (including colds, influenza and yeast infections, among others). Independent laboratory testing of a safe for human use, 25 ppm iodine formula according to this invention against Rhinovirus and Coronavirus (the viruses most frequently responsible for colds and sore throats) demonstrated complete inactivation and 4 log kill in 30 sec (see below). These results clearly support the use of the present invention for treating oral mucosa, throat and nasal passages to prevent or ameliorate colds and sore throats.
Study Results for Development Test RKY01010714.FCAL (A16207) (Feline Calicivirus)
Test Substances: Formula L, Formula I+Ecolab Fruit and Vegetable
Treatment, and Ecolab Fruit and Vegetable Treatment
Test Request Form Number: RKY01010714.FCAL
Project Number: A 16207
Test Substance Preparation: Prepared by Independent Lab
Virus: Feline Calicivirus, Strain F-9 (ATCC VR-782)
Organic Soil Load: 1% fetal bovine serum (FBS)
Exposure Time: 90 seconds
Exposure Temperature: Room temperature (21.0° C.)
Cell Cultures: CRFK (feline kidney cells)
Virus Control Results
Feline Calicivirus=7.25 $\log_{10}$
Cytotoxicity Control Results:
Formula L=Cytotoxicity present at 3.50 $\log_{10}$
Formula L+Ecolab Fruit and Vegetable Treatment=Cytotoxicity present at 2.50 $\log_{10}$
Ecolab Fruit and Vegetable Treatment=No cytotoxicity present ≤1.50 $\text{logo}_{10}$.

The cytotoxicity control is used to determine if the test substance has any cytotoxic effects on the cell cultures used in the study. The percent and log reduction take into account any cytotoxicity observed.
Test Results:
Formula L (Present Invention)
Complete inactivation of the test virus was demonstrated.
A ≥99.98% reduction in viral titer was demonstrated. The log reduction was ≥3.75 $\log_{10}$.
Formula L+Ecolab Fruit and Vegetable Treatment
Complete inactivation of the test virus was demonstrated.
A ≥99.998% reduction in viral titer was demonstrated. The log reduction was ≥4.75 $\log_{10}$.
Ecolab Fruit and Vegetable Treatment
Complete inactivation of the test virus was not demonstrated.
Test virus was detected at 2.25 $\log_{10}$.
A 99.999% reduction in viral titer was demonstrated. The log reduction was 5.00 $\log_{10}$.
Study Results for Development Test RKY01010713.TK.3 IA16206) (*Listeria monocytogenes*)
Test Substance: Formulation L, Formulation L+Ecolab Fruit and Vegetable Treatment, Ecolab Fruit and Vegetable Treatment
Protocol Number: RKY01010713.TK.3
Project Number: A 16206
Test Substance Preparation: Prepared by ATS Labs
Organism: *Listeria monocytogenes* (ATCC 19117)
Exposure Time: 90 seconds
Soil: No organic soil load
Actual Exposure Temp: 20.9° C.
Neutralizer: Letheen Broth with 0.07% Lecithin and 0.5% Tween 80
Carrier Population Control Results: 6.10 $\log_{10}$
All controls were acceptable.
Test Results:
Formulation L (Present Invention): >99.999% (>5.40 log 10) Reduction at 90 seconds
Formulation L+Ecolab Fruit and Vegetable Treatment: >99.999% (>5.40 $\log_{10}$) Reduction at 90 seconds.
Ecolab Fruit and Vegetable Treatment: >99.999% (>5.40 $\log_{10}$) Reduction at 90 seconds
Formulation L, Ecolab Fruit and Vegetable Treatment, and Formulation L+Ecolab Fruit and Vegetable Treatment all demonstrated an identical >99.999% reduction at 90 seconds. All three test substances had identical 100% kill rates on all test recovery plates.
Study Results for Development Test RKY01010713.TK.2 (A162051) (*Escherichia coli*)
Test Substance: Formulation L, Formulation L+Ecolab Fruit and Vegetable Treatment, Ecolab Fruit and Vegetable Treatment
Protocol Number: RKY01010713.TK.2
Project Number: A 16205
Test Substance Preparation: Prepared by ATS Labs
Organism: *Escherichia coli* (ATCC 11229)
Exposure Time: 90 seconds
Soil: No organic soil load
Actual Exposure Temp: 20.9° C.
Neutralizer: Letheen Broth with 0.07% Lecithin and 0.5% Tween 80
Carrier Population Control Results: 6.33 log 10
All controls were acceptable.
Test Results:
Formulation L (Present invention): >99.999% (>5.63 $\log_{10}$) Reduction at 90 seconds
Formulation L+Ecolab Fruit and Vegetable Treatment: >99.999% {>5.63 $\log_{10}$) Reduction at 90 seconds
Ecolab Fruit and Vegetable Treatment: >99.999% (>5.63 log 10) Reduction at 90 seconds
Formulation L, Ecolab Fruit and Vegetable Treatment, and Formulation L+Ecolab Fruit and Vegetable Treatment all demonstrated an identical >99.999% reduction at 90 seconds. All three test substances had identical 100% kill rates on all test recovery plates.
Study Results for Development Test RKY01010713.TK.1 fA16204I (*Salmonella enterica*)
Test Substance: Formulation L, Formulation L+Ecolab Fruit and Vegetable Treatment, Ecolab Fruit and Vegetable Treatment
Protocol Number: RKY01010713.TK.1
Project Number: A 16204
Test Substance Preparation: Prepared by ATS Labs
Organism: *Salmonella enterica* (ATCC 10708)
Exposure Time: 90 seconds
Soil: No organic soil load
Actual Exposure Temp: 20.9° C.
Neutralizer: Letheen Broth with 0.07% Lecithin and 0.5% Tween 80
Carrier Population Control Results: 6.21 log 10
All controls were acceptable.
Test Results:
Formulation L: >99.999% (>5.51 $\log_{10}$) Reduction at 90 seconds
Formulation L+Ecolab Fruit and Vegetable Treatment: >99.999% (>5.51 log 10) Reduction at 90 seconds
Ecolab Fruit and Vegetable Treatment: >99.999% (>5.51 log 10) Reduction at 90 seconds
Formulation L, Ecolab Fruit and Vegetable Treatment, and Formulation L+Ecolab Fruit and Vegetable Treatment all demonstrated an identical >99.999% reduction at 90 seconds. All three test substances had identical 100% kill rates on all test recovery plates.

TABLE 7A

Test Product #1 25 pm
Virus/Strain: Rhinovirus type 14/1059 (ATCC Cat #VR-284)
Host Cell Line: MRC-5 Host Cell Line ATCC #CCL-171

| Dilution (− Log$^{10}$) | Virus Control | Exposure Time 30 Seconds | Cytotoxicity Control | Neuturalization Control | Cell Control (Negative Control) |
|---|---|---|---|---|---|
|  |  |  |  |  | 0000 |
| −2 | NT | CT | ++++ | NT |  |
| −3 | ++++ | 0000 | 0000 | ++++ |  |
| −4 | ++++ | 0000 | 0000 | ++++ |  |
| −5 | ++++ | 0000 | NT | ++++ |  |
| −6 | ++++ | 0000 | NT | +0++ |  |
| −7 | 0000 | 0000 | NT | 0000 |  |
| TCID$_{50}$ (log$_{10}$) | 6.50 | 2.50 | 2.50 | 6.25 |  |
| Log$_{10}$ Reduction | N/A | 4.00 |  | N/A |  |
| Percent Reduction |  | 99.99% |  |  |  |

+ CPE (cytopathic/cytotoxic effect) present
0 CPE (cytopathic/cytotoxic effect) not detected
NT Not Tested
N/A Not Applicable
CT Cytotoxicity
Conclusion: The test product #1 of the present invention completely inactivated Rhinovirus type 14 above the cytotoxicity level following exposure for 30 seconds.

TABLE 7B

Test Product #1 25 pm
Virus/Strain: Coronavirus/229E (ATCC Cat #VR-740)
Host Cell Line: MRC-5 Host Cell Line ATCC #CCL-171

| Dilution (− Log$^{10}$) | Virus Control | Exposure Time 30 Seconds | Cytotoxicity Control | Neuturalization Control | Cell Control (Negative Control) |
|---|---|---|---|---|---|
|  |  |  |  |  | 0000 |
| −2 | NT | CT | ++++ | NT |  |
| −3 | ++++ | 0000 | 0000 | ++++ |  |
| −4 | ++++ | 0000 | 0000 | ++++ |  |
| −5 | ++++ | 0000 | NT | ++++ |  |
| −6 | ++++ | 0000 | NT | ++0 |  |
| −7 | 0000 | 0000 | NT | 0000 |  |
| TCID$_{50}$ (log$_{10}$) | 6.75 | 2.50 | 2.50 | 6.25 |  |
| Log$_{10}$ Reduction | N/A | 4.25 |  | N/A |  |
| Percent Reduction |  | 99.99% |  |  |  |

+ CPE (cytopathic/cytotoxic effect) present
0 CPE (cytopathic/cytotoxic effect) not detected
NT Not Tested
N/A Not Applicable
CT Cytotoxicity
Conclusion: The test product #1 of the present invention completely inactivated Coronavirus strain 229E above the cytotoxicity level following exposure for 30 seconds.

Further Examples—Food Preservation

Two pints of strawberries were treated with the present invention (a solution) by immersing 1 pint of each of the test articles in 300 mL of the 25 ppm solution for 5 minutes. Each of the treated test articles was allowed to air dry at room temperature and then placed in a refrigerator alongside the untreated control articles. At the end of one month, both treated and untreated samples were evaluated. In each case the untreated strawberries were coated with fungi; in contrast, the treated strawberries did not exhibit any fungi and appeared fresh with favorable organoleptic qualities. Furthermore, the treated strawberries exhibited the same luster and firm texture as when they were purchased. The untreated strawberries were dull in color, less firm and began to shrivel. This experiment is just one example of the large range of foods that can be treated with compositions of this application to prevent spoilage.

In yet another experiment, mushrooms were immersed in the same composition as the strawberries for five minutes and allowed to air dry before being placed in the refrigerator alongside the untreated control. The untreated mushrooms began to shrivel, exuding liquid. By the end of one month the untreated mushrooms had lost most of their moisture, had shrunken significantly in volume and had significantly darkened. In contrast to this, the treated mushrooms retained their original texture, color and volume.

In still another experiment, blackberries were treated in the same manner for five minutes as were the strawberries and mushrooms. The treated berries and the untreated control berries were then refrigerated. Initial signs of mold formation were evident on the untreated berries within one week. Mold growth continued under refrigeration until, by the 49$^{th}$ day the untreated berries had softened and were completely overgrown with mold, while the treated berries exhibited no signs of deterioration or mold growth by day 49 when the experiment was terminated.

Example—Spores

The present invention was tested against spores to determine the effectiveness. The present invention was tested at an independent laboratory against *Bacillus subtilis* and *Clostridium sporogenes* at 50 degrees c. and had 0/10 failures on each pathogen, with a 5 min. exposure time according to an EPA protocol. This qualifies the present invention as sporicidal. The present compositions are also effective against spores at room temperature, but exposure is generally for a longer period of time. To inhibit and/or eliminate spores on surfaces or in solution, compositions often are used at a temperature between about 5 degrees and 58 degrees Celsius.

The formula used was the same one for all of our standard testing. This is significant, since no other intermediate level hospital grade disinfectant can make such a claim. The present compositions have efficacy against the same EPA required spores at room temperature, having been evaluated and having demonstrated spore kill at 10 min. on porcelain penicylinders according to an EPA protocol.

The invention claimed is:

1. An aqueous composition consisting essentially of an antimicrobial effective amount of uncomplexed molecular iodine ($I_2$), a source of Wide ($I^-$) in an effective amount, a source of iodate ($IO_3$—) in an effective amount and a predetermined amount of an acid, wherein the resulting molar ratio of molecular iodine to iodate in said composition ranges from 0.1 to 25 to 1.5 to 5.0 and the concentration of acid in the composition is effective to provide a buffering pH ranging from 1.5 to 6.5, the composition providing a stable concentration of molecular iodine within the range of 0.5 ppm to 2500 ppm for a period of at least 2 weeks to 5 years.

2. The composition according to claim 1 wherein the molar ratio of iodide to iodate ranges from 1.25 to 5 to 1.5 to 15.0.

3. The composition according to claim 1 wherein the molar ratio of iodide to iodate ranges from 1.25 to 5.0 to 0.5 to 7.5.

4. The composition according to claim 1 wherein the source of iodide is selected from the group consisting of sodium iodide, potassium iodide, lithium iodide, calcium iodide, magnesium iodide, hydroiodic acid and mixtures thereof and the source of iodate is selected from the group consisting of sodium iodate, potassium iodate, lithium iodate, calcium iodate, magnesium iodate, hydroiodic acid and mixtures thereof.

5. The composition according to claim 4 wherein the source of iodide is sodium iodide, potassium iodide and mixtures thereof, and the source of iodate is sodium iodate, potassium iodate and mixtures thereof.

6. The composition according to claim 1 wherein the source of iodide is selected from the group consisting of sodium iodide, potassium iodide and mixtures thereof.

7. The composition according to claim 1 wherein the source of iodate is selected from the group consisting of sodium iodate, potassium iodate and mixtures thereof.

8. The composition according to claim 1 wherein hydroiodic acid is used to complement the source of iodide.

9. The composition according to claim 1 wherein the concentration of uncomplexed molecular iodine ranges from 1 ppm to 500 ppm.

10. The composition according to claim 1 wherein the concentration of uncomplexed molecular iodine ranges from 20 ppm to 350 ppm.

11. The composition according to claim 1 wherein the concentration of uncomplexed molecular iodine ranges from 10 ppm to 300 ppm.

12. The composition according to claim 1 further comprising at least one other germicidal agent.

13. The composition according to claim 12 wherein said other germicidal agent is selected from the group consisting of a peroxide disinfectant, ethanol, isopropanol, propanol, octanoic acid, caprylic acid or mixtures thereof.

14. The composition according to claim 13 wherein said peroxide disinfectant is selected from the group consisting of peracetic acid, hydrogen peroxide, benzoyl peroxide and mixtures thereof.

15. The composition according to claim 1 further comprising at least one further component selected from the group consisting of non-aqueous solvents, surfactants, emulsifiers, emollients, oils, humectants, conditioning agents, thickeners/thickening agents, medicaments, fragrances, preservatives, skin protecting agents, pigments, dyes, coloring agents and mixtures thereof.

16. The composition according to claim 1 adapted for application to a surface.

17. The composition according to claim 1 adapted for application to keratinous or mucosal tissue.

18. The composition according to claim 1 adapted for application to keratinous or mucosal tissue including subgingival pockets and periodontal spaces as a liquid, gel, paste, cream, lotion, solid, stream or spray for transient effect or extended residence times.

19. The composition according to claim 1 which includes a gelling agent and said composition is adapted for application to a periodontal surface.

20. The composition according to claim 1 which includes a gelling agent and said composition is adapted for inclusion in a permeable package which releases molecular iodine from said packaging into a surrounding environment.

21. A composition according to claim 1 adapted as a mouthwash composition.

* * * * *

UNITED STATES PATENT AND TRADEMARK OFFICE
CERTIFICATE OF CORRECTION

PATENT NO. : 10,092,006 B2
APPLICATION NO. : 15/128556
DATED : October 9, 2018
INVENTOR(S) : Rodger Elliot Kolsky, Herbert Moskowitz and Jack Kessler It is certified that error appears in the above-identified patent and that said Letters Patent is hereby corrected as shown below:

In the Claims

On Column 45, Line 31, in Claim 1, "a source of Wide" should read "a source of iodide".

Signed and Sealed this
Twenty-seventh Day of February, 2024

Katherine Kelly Vidal
*Director of the United States Patent and Trademark Office*